US012622904B2

(12) United States Patent
Nasser et al.

(10) Patent No.: US 12,622,904 B2
(45) Date of Patent: *May 12, 2026

(54) BUPRENORPHINE DOSING REGIMENS

(71) Applicant: INDIVIOR UK LIMITED, Hull (GB)

(72) Inventors: Azmi Nasser, North Chesterfield, VA (US); Celine M. Laffont, North Chesterfield, VA (US); Christian A. Heidbreder, North Chesterfield, VA (US)

(73) Assignee: INDIVIOR UK LIMITED, Hull (GB)

( * ) Notice: Subject to any disclaimer, the term of this patent is extended or adjusted under 35 U.S.C. 154(b) by 0 days.

This patent is subject to a terminal disclaimer.

(21) Appl. No.: 19/085,650

(22) Filed: Mar. 20, 2025

(65) Prior Publication Data

US 2025/0213553 A1    Jul. 3, 2025

Related U.S. Application Data

(63) Continuation of application No. 17/985,253, filed on Nov. 11, 2022, which is a continuation of application No. 17/217,914, filed on Mar. 30, 2021, now Pat. No. 11,839,611, which is a continuation of application No. 15/523,986, filed as application No. PCT/IB2015/002269 on Nov. 6, 2015, now Pat. No. 11,000,520.

(60) Provisional application No. 62/199,778, filed on Jul. 31, 2015, provisional application No. 62/112,546, filed on Feb. 5, 2015, provisional application No. 62/100,391, filed on Jan. 6, 2015, provisional application No. 62/076,854, filed on Nov. 7, 2014.

(51) Int. Cl.
| | |
|---|---|
| *A61K 31/485* | (2006.01) |
| *A61K 9/00* | (2006.01) |
| *A61K 47/22* | (2006.01) |
| *A61K 47/34* | (2017.01) |

(52) U.S. Cl.
CPC .......... *A61K 31/485* (2013.01); *A61K 9/0019* (2013.01); *A61K 47/22* (2013.01); *A61K 47/34* (2013.01)

(58) Field of Classification Search
CPC .... A61K 31/485; A61K 9/0019; A61K 47/22; A61K 47/34
See application file for complete search history.

(56) References Cited

U.S. PATENT DOCUMENTS

| | | | |
|---|---|---|---|
| 4,599,354 A | 7/1986 | Shulman | |
| 4,804,663 A | 2/1989 | Kennis et al. | |
| 4,938,763 A | 7/1990 | Dunn et al. | |
| 5,324,519 A | 6/1994 | Dunn et al. | |
| 5,346,903 A | 9/1994 | Ackerman et al. | |
| 5,453,425 A | 9/1995 | François et al. | |
| 5,486,362 A | 1/1996 | Kitchell et al. | |
| 5,616,587 A | 4/1997 | François et al. | |
| 5,648,093 A | 7/1997 | Gole et al. | |
| 5,688,801 A | 11/1997 | Mesens et al. | |
| 5,702,716 A | 12/1997 | Dunn et al. | |
| 5,744,153 A | 4/1998 | Yewey et al. | |
| 5,770,231 A | 6/1998 | Mesens et al. | |
| 5,792,477 A | 8/1998 | Rickey et al. | |
| 5,990,194 A | 11/1999 | Dunn et al. | |
| 6,224,905 B1 | 5/2001 | Lawrence et al. | |
| 6,261,583 B1 | 7/2001 | Dunn et al. | |
| 6,264,987 B1 | 7/2001 | Wright et al. | |
| 6,528,080 B2 | 3/2003 | Dunn et al. | |
| 6,565,874 B1 | 5/2003 | Dunn et al. | |
| 6,596,316 B2 | 7/2003 | Lyons et al. | |
| 6,630,155 B1 | 10/2003 | Chandrashekar et al. | |
| 7,041,320 B1 | 5/2006 | Nuwayser | |
| 7,824,700 B2 | 11/2010 | Cleland et al. | |
| 8,173,148 B2 | 5/2012 | Dadey et al. | |
| 8,221,778 B2 | 7/2012 | Siegel et al. | |
| 8,236,292 B2 | 8/2012 | Thuresson et al. | |
| 8,236,755 B2 | 8/2012 | Thuresson et al. | |
| 8,313,763 B2 | 11/2012 | Margaron et al. | |
| 8,324,343 B2 | 12/2012 | Moore et al. | |
| 8,329,203 B2 | 12/2012 | Siegel et al. | |
| 8,475,832 B2 | 7/2013 | Myers et al. | |
| 8,501,216 B2 | 8/2013 | Cleland et al. | |
| 8,545,832 B2 | 10/2013 | Thuresson et al. | |
| 8,852,638 B2 | 10/2014 | Luk et al. | |
| 8,889,782 B2 | 11/2014 | Fung et al. | |
| 8,921,387 B2 | 12/2014 | Norton et al. | |
| 8,975,270 B2 | 3/2015 | Norton et al. | |

(Continued)

FOREIGN PATENT DOCUMENTS

| | | |
|---|---|---|
| GB | 784659 A | 10/1957 |
| WO | 9119474 A1 | 12/1991 |

(Continued)

OTHER PUBLICATIONS

Graves, R.A., et al., "InVitro Dissolution Method for Evaluation of Buprenorphine in Situ Gel Formulation: A Technical Note," AAPS PharmSciTech, vol. 8(3), Article 62, pp. E1 to E4 (2007).

Greenwald et al., "Buprenorphine Duration of Action: Mu-opioid Receptor Availability and Pharmacokinetic and Behaviorial Indices," Biological Psychiatry, Elsevier Science, New York, NY; US, vol. 61, No. 1, Dec. 8, 2006 (Dec. 8, 2006), pp. 101-110, XP005798784.

Greenwald, M.K., et al., "Effects of buprenorphine sublingual tablet maintenance on opioid drug-seeking behavior by humans," Psychopharmacology (Berl), 2002; 160:344-352.

Grerenwald, M.K., et al., "Sustained release d-amphetamine reduces cocaine but not 'speedball'-seeking in buprenorphine-maintained volunteers: a test of dual-agonist pharmacotherapy for cocaine/heroin polydrug abusers," Neuropsychopharmacology, 2010;35:2624-2637.

(Continued)

*Primary Examiner* — Adam C Milligan
*Assistant Examiner* — William Y Lee
(74) *Attorney, Agent, or Firm* — The Marbury Law Group, PLLC

(57) ABSTRACT

The disclosure provides a dosage regimen using sustained-release buprenorphine formulations to produce therapeutic levels of buprenorphine in patients for the treatment of pain or opioid use disorders.

9 Claims, No Drawings

(56) References Cited

U.S. PATENT DOCUMENTS

| | | | | |
|---|---|---|---|---|
| 9,044,450 | B2 | 6/2015 | Luk et al. | |
| 9,272,044 | B2 | 3/2016 | Norton et al. | |
| 9,295,645 | B2 | 3/2016 | Norton et al. | |
| 9,498,432 | B2 | 11/2016 | Norton et al. | |
| 9,782,402 | B2 | 10/2017 | Norton et al. | |
| 9,827,241 | B2 | 11/2017 | Norton et al. | |
| 11,000,520 | B2 * | 5/2021 | Nasser | A61K 47/34 |
| 11,839,611 | B2 * | 12/2023 | Nasser | A61K 47/22 |
| 2003/0004100 | A1 | 1/2003 | Dasch et al. | |
| 2003/0211157 | A1 | 11/2003 | Simon | |
| 2004/0018238 | A1 | 1/2004 | Shukla | |
| 2004/0033250 | A1 | 2/2004 | Patel et al. | |
| 2004/0101557 | A1 | 5/2004 | Gibson et al. | |
| 2004/0151670 | A1 | 8/2004 | Blondino et al. | |
| 2005/0032781 | A1 | 2/2005 | Ehrich | |
| 2005/0048115 | A1 | 3/2005 | Mangena et al. | |
| 2005/0048123 | A1 | 3/2005 | Su et al. | |
| 2005/0079202 | A1 | 4/2005 | Chen et al. | |
| 2005/0106214 | A1 | 5/2005 | Chen | |
| 2006/0000297 | A1 | 1/2006 | Ashammakhi et al. | |
| 2006/0210604 | A1 | 9/2006 | Dadey et al. | |
| 2007/0011782 | A1 | 1/2007 | Georges et al. | |
| 2007/0077304 | A1 | 4/2007 | Luk et al. | |
| 2007/0265190 | A1 | 11/2007 | Thuresson et al. | |
| 2008/0299168 | A1 | 12/2008 | Dadey et al. | |
| 2009/0061011 | A1 | 3/2009 | Talton | |
| 2009/0092650 | A1 | 4/2009 | Warren et al. | |
| 2010/0266655 | A1 | 10/2010 | Dadey | |
| 2010/0292195 | A1 | 11/2010 | Dadey et al. | |
| 2013/0071477 | A1 | 3/2013 | Fischer | |
| 2013/0190341 | A1 | 7/2013 | Tiberg et al. | |
| 2013/0202658 | A1 | 8/2013 | Norton et al. | |
| 2013/0203796 | A1 | 8/2013 | Norton et al. | |
| 2013/0210853 | A1 | 8/2013 | Norton et al. | |
| 2014/0193347 | A1 | 7/2014 | Thuresson et al. | |
| 2015/0064118 | A1 | 3/2015 | Thuresson et al. | |
| 2015/0182522 | A1 | 7/2015 | Tiberg et al. | |
| 2015/0231258 | A1 | 8/2015 | Luk et al. | |
| 2016/0128997 | A1 | 5/2016 | Nasser | |
| 2017/0079976 | A1 | 3/2017 | Norton et al. | |
| 2017/0281518 | A1 | 10/2017 | Norton et al. | |
| 2017/0354653 | A1 | 12/2017 | Nasser | |
| 2018/0243292 | A1 | 8/2018 | Nasser | |
| 2018/0360821 | A1 | 12/2018 | Laffont et al. | |

FOREIGN PATENT DOCUMENTS

| | | | |
|---|---|---|---|
| WO | 1995027481 | A1 | 10/1995 |
| WO | 0006117 | A1 | 2/2000 |
| WO | 2000024374 | A1 | 5/2000 |
| WO | 0115699 | A1 | 3/2001 |
| WO | 2001035929 | A3 | 12/2001 |
| WO | 2002030393 | A3 | 6/2002 |
| WO | 2003041684 | A3 | 9/2003 |
| WO | 2004043432 | A3 | 7/2004 |
| WO | 2004081196 | A2 | 9/2004 |
| WO | 2005048989 | A1 | 6/2005 |
| WO | 2006053175 | A2 | 5/2006 |
| WO | 2007041410 | A3 | 7/2007 |
| WO | 2007061828 | A3 | 7/2007 |
| WO | 2007103185 | A3 | 3/2008 |
| WO | 2008045516 | A1 | 4/2008 |
| WO | 2008100532 | A1 | 8/2008 |
| WO | 2006041942 | A3 | 4/2009 |
| WO | 2008153611 | A3 | 7/2009 |
| WO | 2009091737 | A3 | 5/2010 |
| WO | 2011154725 | A3 | 6/2012 |
| WO | 2011154724 | A9 | 8/2012 |
| WO | 2014016428 | A1 | 1/2014 |
| WO | 2014144241 | A1 | 9/2014 |
| WO | 2015136253 | A1 | 9/2015 |
| WO | 2016066655 | A1 | 5/2016 |
| WO | 2016071767 | A1 | 5/2016 |
| WO | 2016102683 | A1 | 6/2016 |
| WO | 2017046384 | A1 | 3/2017 |
| WO | 2018229551 | A3 | 2/2019 |

OTHER PUBLICATIONS

Greenwald, M.K., et al., "Effects of buprenorphine maintenance dose on mu-opioid receptor availability, plasma concentrations, and antagonist blockade in heroin-dependent volunteers," Neuropsychopharmacology 28 (911):2000-2009 (Nov. 2003).

Greenwald, M.K., et al., (Nov. 1, 2014, e-published Aug. 19, 2014), "Buprenorphine maintenance and muopioid receptor availability in the treatment of opioid use disorder: implications for clinical use and policy," Drug Alcohol Depend 144:1-11.

Griffeth, R.J., et al., (2002), "Is Lucteal Production of PGF2a Required for Luteolysis?," Biology of Reproduction 66 (Supplement 1), Abstract 465, 2 pages.

Hempel, G., et al., "Cytotoxicity of dimethylacetamide and pharmacokinetics in children receiving intravenous busulfan," J. Cli. Oncol., 25(13):1772-1778 (May 1, 2007).

Henriksen, G., et al., (May 2008, e-published Nov. 29, 2007). "Imaging of opioid receptors in the central nervous system," Brain 131(Pt. 5):1171-1196.

Hillhouse, M., et al., (Sep. 2011), "Participant characteristics and buprenorphine dose," Am J. Drug Alcohol Abuse 37(5):453-459.

Hoffman, K., et al., (May/Jun. 2017),"Safety of a Rapidly Dissolving Buprenorphine/Naloxone Sublingual Tablet (BNX-RDT) for Treatment of Opioid Dependence: A Multicenter, Open-label Extension Study," J. Addict. Med. 11 (3):217-223.

Hser, Y., et al., (Jan. 2014, e-published Oct. 9, 2013), "Treatment retention among patients randomized to buprenorphine/naloxone compared to methadone in a multi-site trial," Addiction 109(1):79-87.

Indivior Announces Postive Top-Line Phase 3 Pivotal Study Results for RBP-6000 Buprenophone Monthly Depot for the Treatment of Opioid Use Disorder, 7 pages (Aug. 17, 2016) [Retrieved from: http://www.indivior/investor-news/rbp-6000-phase-3-top-line-results].

International Search Report mailed on Dec. 12, 2018, for PCT Application No. PCT/IB2018/000770, filed Jun. 15, 2018, 6 pages.

International SR/WO issued on Mar. 24, 2016 for PCT Application No. PCT/IB2015/002269, filed on Nov. 6, 2015, 5 pages.

International SR/WO issued on Jun. 11, 2015, for PCT Application No. PCT/GB2015/050676, filed on Mar. 9, 2015, 6 pages.

Jain, R.A., (Dec. 2000), "The manufacturing techniques of various drug loaded biodegradable poly(lactide-coglycolide) (PLGA) devices," Biomaterials 21 (23):2475-2490.

Jarr, E.M., et al., (Jul. 1999), "Sustained Release of Lidocaine from an Injectable Implant System for Treatment of Post-Operative," Proceedings Int'l Symp. Control RE/Bioact Materials, Abstract #5423, 4 pages.

Johanson, C.E., et al., "Diversion and abuse of buprenorphine: findings from national surveys of treatment patients and physicians," Drug Alcohol Depend, 120(1-2):190-195 (2012).

Johnson, B., et al., "Diversion of methadone and buprenorphine by patients in opioid substitution treatment in Sweden: prevalence estimates and risk factors," Int. J. Drug Policy, 26(2):183-190 (Feb. 2015, e-published Oct. 30, 2014).

Johnson, O.L., et al., "The stabilization and encapsulation of human growth hormone into biodegradable microspheres," Pharm res., 14(6):730-735 (Jun. 1997).

Kampman, K., et al., "American Society of Addiction Medicine (ASAM) National Practice Guideline for the Use of Medications in the Treatment of Addiction Involving Opioid Use," J. Addict Med., 9(5):358-367 (2015.

Kaul, S., et al., "Polymeric-based perivascular delivery of a nitric oxide donor inhibits intimal thickening after balloon denudation arterial injury: role of nuclear factor kappaB," J. Am Coli Cardio, 35(2):493-501 (Feb. 2000).

Kissel, T., "ABA-triblock copolymers from biodegradable polyester A-blocks and hydrophilic poly(ethylene oxide) B-blocks as a can-

(56) References Cited

OTHER PUBLICATIONS didate for in situ forming hydrogel delivery systems for proteins," Adv. Drug Deliv. Rev., 54(1):99-134.

Kranz, H., et al., "Myotoxidity studies of injectable biodegradable in-situ forming drug delivery systems," Int. J. Pharm., 212(1):11-18 (Jan. 5, 2001).

Kuhlman, J.J., et al. (Apr. 1998), "Relationship of plasma buprenorphine and norbuprenorphine to withdrawal symptoms during dose induction, maintenance and withdrawal from sublingual buprenorphine," Addiction 93 (4):549-559.

Laffont, C.M., et al., "Population Pharmacokinetic Modeling After Repeated Administrations of RBP-6000, a New, Subcutaneously Injectable, Long-Acting, Sustained-Release Formulation of Buprenorphine, for the Treatment of Opioid Use Disorder," J. Clin. Pharmacol, 56(7):806-815 (Jul. 2016, e-published Mar. 11, 2016).

Lee, K.P., et al., "Toxicity of N-methyl-2-pyrrolidone (NMP): teratogenic, subchronic, and two-year inhalation studies," Fundam Appl. Toxicol., 9(2):222-235 (Aug. 1987).

Lester, P.A., Traynor, J.R., "Comparison of the in vitro efficacy of mu, delta, kappa and ORLI receptor agonists and non-selective opioid agnoists in dog bran membranes," Brain Res., 2006, 1073-1074:290-296.

Lewis, J.W., Buprenorphine, Drug Alcohol Depend. 1985; 14:363-372.

Liao, Chuang-Liang et al., "In Vitro Skin Permeation of Buprenorphine Transdermal Patch," Journal of Food and Drug Analysis, Taibei, TW, 16(6):8-15 (Dec. 1, 2008).

Lindhardt et al., "Intranasal Absorption of Buprenorphine—in vivo biovavailabity study in sheep," Int. J. Pharm., 205 (1-2):159-163 (2000).

Ling W., Charuvastra C., Collins, J.F., Batki S., Brown L.S., Jr., Kintaudi, P., Wesson D.R., McNicholas L., Tusel D.J., Malkemerker, U., Renner J.A., Jr., Santos E., Casadonte, P., Fye, C., Stine, S., Wang, R.I., Segal, D., "Buprenorphine maintenance treatment of opiate dependence: a multicenter, randomized clinical trial," Addiction, 1998; 93:475-486.

Ling, W., Wesson, D.R., Charuvastra, C., Klett, C.J., "A controlled trial comparing buprenorphine and methadone maintenance in opioid dependence," Arch. Gen. Psychiatry, 1996; 53:401-407.

Ling, W., et al., (Oct. 13, 2010), "Buprenorphine implants for treatment of opioid dependence: a randomized controlled trial," JAMA 304(14):1576-1583.

Li, M., et al., "A novel, non-prostanoid EP2 receptor-selective prostaglandin E2 agonist stimulates local bone formation and enhances fracture healing," Bone Miner Res., 18(11):2033-2042 (Nov. 2003).

Lofwall, M.R., et al., "Inability to access buprenorphine treatment as a risk factor for using diverted buprenorphine," Drug Alcohol Depend., 126(3):379-383 (Dec. 1, 2012, e-published Jun. 15, 2012).

Lutfy K., Cowan A., "Buprenorphine: a unique drug with complex pharmacology," Curr. Neurophamacol, 2004; 2:395-402.

Lynch, G.S., et al., "Emerging drugs for sarcopenia: age-related muscle wasting," Expert Opin Emerg Drugs., 9 (2):345-361 (Nov. 2004).

Makadia, H.K., et al., "Poly Lactic-coGlycolic Acid (PLGA) as Biodegradable Controlled Drug Delivery Carrier," Polymers, 3(3):1377-1397 (Sep. 1, 2011, e-published Aug. 26, 2011).

Malik, K., et al., (2010), "Atrigel: A Potential Parenteral Controlled Drug Delivery System," Der Pharmacia Sinica 1(1):74-81.

Matschke, C., et al., "Sustained-release injectables formed in situ and their potential use for veterinary products," J. Control Release, 85(1-3):1-15 (Dec. 2007).

Matthes, H.W., Maldonado, R., Simonin, F, Valverde, O, Slowe, S., Kitchen, I, Befort, K., Kierich A., Le Meur, M. Dolle, P., Tzavara, E., Hanoune, J., Roques, B.P., Kieffer, B.L., "Loss of morphine-induced analgesia, reward effect and withdrawal symptoms in mice lacking the mu-opioid-receptor gene," Nature 1996, 383:819-823.

McLeod, D.C., et al., "Hormonal therapy: historical perspective to future directions," Urology 61 (Suppl2A):3-7 (Feb. 2003).

Mealy (2004), "Treatment of Metabolic Disorders by Condition," Annual Update 2003/2004 Drugs of the Future, 29 (8):843-872.

Medicott, N.J., et al., "Sustained release veterinary parenteral products," Adv. Drug Deliv. Rev., 56(10):1345-1365.

Miller, R.A., et al., "Degradation rates of oral resorbable implants (polylactates and polyglycolates): rate modification with changes in PLA/PGA copolymer ratios," Biomed Mater Res, 11(5):711-719 (Sep. 1977).

Mottu, F., et al., "In vitro assessment of new embolic liquids prepared from preformed polymers and water-miscible solvents for aneurysm treatment," Biomaterials, 21(8):803-811 (Apr. 2000).

Nasser, Azmi F., et al., "A Population Pharmacokinetic and Pharmacodynamic Modelling Approach to Support the Clinical Development of RBP-6000, a New, Subcutaneously Injectable, Long-Acting, Sustained-Release Formulation of Buprenorphine, for the Treatment of Opioid Dependence," Clinical Pharmacokinetics, Adis International Ltd., Auckland, NZ, vol. 53, No. 9, Sep. 1, 2014 (Sep. 1, 2014), p. 813-824, XP009189013.

Nasser, A.F., et al., (Aug. 2015, e-published Jan. 21, 2015), "Pharmacokinetics of Sublingual Buprenorphine and Naloxone in Subjects with Mold to Severe Hepatic Impairment (Child-Pugh Classes A, B, and C), in Hepatitis C Virus-Seropositive Subjects, and in HealthyVolunteers," Clin Pharmacokinet 54(8):837-849.

Nasser, A.F., et al., "Sustained-Release Buprenorphine (RBP-6000) Blocks the Effects of Opioid Challenge with Hydromorphone in Subjects with Opioid Use Disorder," Journal of Clinical Psychopharmacology 35(1):18-26, (Feb. 2016.).

Packhaeuser, C.B., et al., (Sep. 2004), "In situ forming parenteral drug delivery systems: an overview," Eur J Pharm Biopharm 58(2):445-455.

Panaccione, C., et al., "Use of a Trinomial Distribution Probability Model in Development of a Tier-Testing Scheme for Content Uniformity Testing," Drug Information Journal, 31:903-90 (1997).

Paralkar, V.M., et al., "An EP2 receptorselective prostaglandin E2 agonist induces bone healing," PNAS USA, 100(11):6736-6740 (May 27, 2003, e-published May 14, 2003).

Parent, M., et al., "PI-GA in situ implants formed by phase inversion: critical phycicochemical parameters to modulate drug release," J. Control Release, 172(1):292-304 (Nov. 28, 2013, e-published Sep. 1, 2013.

Patel, R.B., et al., "Effect of injection site implant formation and drug release in vivo," J. Control Release, 147(3):350-358, (Nov. 1, 2010, e-published Aug. 20, 2010).

Pechenov, S., et al., "Injectable controlled release formulations incorporating protein crystals," J Control Release, 96(1):1 49-158 (Apr. 16, 2004.

Perez-Marreno, R., "A six-month, open-label study assessing a new formulation of leuprolide 7.5 mg for suppression of testosterone in patients with prostate cancer," Clinical Therapuetics, 24(11):1902-1914 (Nov. 2002).

Perez-Marrero, R., et al., "A subcutaneous delivery system for the extended release of leuprolide acetate for the treatment of prostate cancer," Expert Opin Pharmacother., 5(2):447-457 (Feb. 2004).

Radomsky, M.L., et al., "The Controlled Release of Ganirelix from the Atrigel TM Injectable Implant System," Proceed Intem Symp Control Re/Bioact Mater., 20:458-459 (1993).

Rathbone, M.J., et al., "Modified release drug delivery in veterinary medicine," Drug Discov. Today, 7(15):823-829 (Aug. 1, 2002).

Ravivarapu, H.B., et al., "Sustained activity and release of leuprolide acetate from an in situ forming polymeric implant," AAPS PharmSciTech 1(1):E1 (Feb. 28, 2000).

Ravivarapu, H.B., et al., "Parameters affecting the efficacy of a sustained release polymeric implant of leuprolide," Int. J. Pharm., 194(2):181-191 (Jan. 25, 2000).

Ravivarapu, H.B.,m et al., "Sustained suppression of pituitary-gonadal axis with an injectable, in-situ forming implant of leuprolide acetate," J. Pharm Sci., 89(6):732-741 (Jun. 2000).

Reckitt Benckiser Pharmaceuticals, Inc., "A Multiple-Dose Study of Blockade of Subjective Opioid Effects, Plasma Levels, and Safety of Subcutaneous Injections of Depot Buprenorphine (RBP-6000) in Subjects with Opioid Use Disorder," ClinicalTrials.Gov., Identifier: NCT-2044094, Jan. 22, 2014.

Reckitt Benckiser Pharmaceuticals, Inc., "A Multiple-Dose Study of Blockade of Subjective Opioid Effects, Plasma Levels, and Safety

(56) References Cited

OTHER PUBLICATIONS of Subcutaneous Injections of Depot Buprenorphine (RBP-6000) in Subjects With Opioid Use Disorder," ClinicalTrials. Gov, Identifier: NCT02044094, Jan. 27, 2014.

Reckitt Benckiser Pharmaceuticals, Inc., "A Mutiple-Dose Study of Blockade of Subjective Opioid Effects, Plasma Levels, and Safety of Subcutaneous Injections of Depot Buprenorphine (RBP-6000) in Subjects With Opioid Use Disorder," ClinicalTrials.Gov, Identifier: NCT02044094, Sep. 28, 2014.

Reckitt Benckiser Pharmaceuticals, Inc., "A Multiple-Dose Study of Blockade of Subjective Opioid Effects, Plasma Levels, and Safety of Subcutaneous Injections of Depot Buprenorphine (RBP-6000) in Subjects With Opioid Use Disorder," ClinicalTrials. Gov, Identifier: NCT02044094, Feb. 17, 2015.

Reckitt Benckiser Pharmaceuticals, Inc., "A Multiple-Dose Study of Blockade of Subjective Opioid Effects, Plasma Levels, and Safety of Subcutaneous Injections of Depot Buprenorphine (RBP-6000) in Subjects With Opioid Use Disorder," ClinicalTrials.Gov, Identifier: NCT02044094, Aug. 21, 2015.

Reckitt Benckiser Pharmaceuticals, Inc., "An Open-Label, Multi-center, Multiplecenter, Multiple Dose Study of the Safety, Tolerability, Pharmacokinetics, and Efficacy Markers of Subcutaneous Injections of Depot Buprenorphine (RBP-6000) in Treatment Seeking Opioid-Dependent Subjects," ClinicalTrials.Gov, Identifier: NCT01738503, Nov. 29, 2012.

Reckitt Benckiser Pharmaceuticals, Inc., "An Open-Label, Multi-center, Multiplecenter, Multiple Dose Study of the Safety, Tolerability, Pharmacokinetics, and Efficacy Markers of Subcutaneous Injections of Depot Buprenorphine (RBP-6000) in Treatment Seeking Opioid-Dependent Subjects," ClinicalTrials.Gov, Identifier: NCT01738503, Jul. 29, 2013.

Reckitt Benckiser Pharmaceuticals, Inc., "An Open-Label, Multi-center, Multiplecenter, Multiple Dose Study of the Safety, Tolerability, Pharmacokinetics, and Efficacy Markers of Subcutaneous Injections of Depot Buprenorphine (RBP-6000) in Treatment Seeking Opioid-Dependent Subjects," ClinicalTrials.Gov, Identifier: NCT01738503, Jan. 15, 2014.

Reckitt Benckiser Pharmaceuticals, Inc., "An Open-Label, Multi-center, Multiplecenter, Multiple Dose Study of the Safety, Tolerability, Pharmacokinetics, and Efficacy Markers of Subcutaneous Injections of Depot Buprenorphine (RBP-6000) in Treatment Seeking Opioid-Dependent Subjects," ClinicalTrials.Gov, Identifier: NCT01738503, Sep. 28, 2014.

Reckitt Benckiser Pharmaceuticals, Inc., "An Open-Label, Multi-center, Multiplecenter, Multiple Dose Study of the Safety, Tolerability, Pharmacokinetics, and Efficacy Markers of Subcutaneous Injections of Depot Buprenorphine (RBP-6000) in Treatment Seeking Opioid-Dependent Subjects," ClinicalTrials.Gov, Identifier: NCT01738503, Jun. 3, 2015.

Reckitt Benckiser Pharmaceuticals, Inc., "An Open-Label, Multi-center, Multiplecenter, Multiple Dose Study of the Safety, Tolerability, Pharmacokinetics, and Efficacy Markers of Subcutaneous Injections of Depot Buprenorphine (RBP-6000) in Treatment Seeking Opioid-Dependent Subjects," ClinicalTrials.Gov, Identifier: NCT01738503, Aug. 6, 2015.

Romero-Gonzalez, M., et al., (Dec. 2017, e-published Nov. 16, 2017), "Buprenorphine-naloxone treatment responses differ between young adults with heroin and prescription opioid use disorders," Am J Addict 26(8):838-844.

Rosen, M.I., et al., "Buprenorphine: duration of blockade of effects of intramuscular hydromorphone," Drug Alcohol Depend. 1994; 35:141-149.

Rosenthal, R.N., et al., (Dec. 2013, e-published Sep. 18, 2013), "Buprenorphine implants for treatment of opioid dependence: randomized comparison to placebo and sublingual buprenorphine/naloxone," Addiction 108 (12):2141-2149.

Saxon, A.J., et al., "Buprenorphine/Naloxone and methadone effects on laboratory indices of liver health: a randomized trial," Drug Alcohol Depend, 128(1-2):71-76 (2013).

Schoenhammer, K., et al., "Injectable in situ forming depot systems: PEG-DAE as novel solvent for improved PLGA storage stability," Int. J. Pharm., 371(1-2):33-39 (Apr. 17, 2009, e-published Dec. 24, 2008).

Schoenhammer, K., et al., (Dec. 2009, e-published Oct. 1, 2009), "Poly(ethyleneglycol) 500 dimethylether as novel solvent for injectable in situ forming depots," Pharm Res, 26(12):2568-2577.

Schulman, C.C., "LHRH Agonists in Prostate Cancer Optimising Testosterone Control with Eligard," European Urology Supplements, 4:1-3 (2005).

Schwach-Abdellaout, K., et al., "Local delivery of antimicrobial agents for the treatment of periodontal diseases," Eur J Pharm Biopharm., 50(1):83-99 (Jul. 2000).

Shargel et al., Appendix B: Applications of Computers in Pharmacokinetics, Applied Biopharmaceutics & Pharmacokinetics, Fourth Edition, Appleton & Lang, pp. 653-660, 1999.

Sherman, J.M., et al., "Localized Delivery of Bupivacaine HCL from Astrigel TM Formulations for the Management of Postoperative Pain," Pharmaceutical Research, 11(10), PDD7574, 2 pages (1994).

Shukla V.K., et al. (1991), "Antagonism of acute cocaine toxicity by buprenorphine," Life Sci., 49(25):1887-1893.

Sigmon et al., "An injection depot formulation of buprenorphine: extended biodelivery and effects," Addiction, 101:420-432 (2006).

Sigmon, S.C., et al., "Evaluation of an injection depot formulation of buprenorphine: placebo comparison," Addiction, 2004; 99:1439-1449.

Sinha, V.R., et al., "Poly-epsilon-caprolactone microspheres and nanospheres: an overview," Int J Pharm., 278 (1):1-23 (Jun. 18, 2004).

Smith, R.W., et al., "A Study of Water Diffusion, in Both Radial and Axial Directions, into Biodegradable Monolithic Depots Using Ion Beam Analuysis," Polymer, 45:4893-4908 (2004).

Sobel et al., "Open-label trial of an injection depot formulation of buprenorphine in opioid detoxification," Drug and Alcohol Dependence, 73: Nov. 22, 2004.

Southard, G.L., et al., "Subgingival controlled release of antimicrobial agents in the treatment of periodontal disease," Int J Antimicrob Agents, 9(4):239-253 (Feb. 1998).

Southard, G.L., et al., "The drug delivery and biomaterial attributes of the Atrigel technology in the treatment of periodontal disease," Expert Opin Investig Drugs, 7(9):1483-1491 (Sep. 1998).

Strain et al., "Blockade of hydromorphone effects by buprenorphine/naloxone and buprenorphine," Psychopharmacoloy, vol. 159, pp. 161-166 (2002).

Sublocade, Highlights of Prescribing Information (2002), 39 pages.

Suboxone, Highlights of Prescribing Information (2002), revised Feb. 2018), 31 pages.

Subutex, Highlights of Prescribing Information (2002, revised Dec. 2011, revised Mar. 2018) 14 pages.

Sundaram, S., et al., "Peptides: Nasal and Pulmonary Delivery of Deslorelin, a Peptide Drug," American Pharmaceutical Review, 130-139 (2004).

Swanson, B.N., "Medical use of dimethyl sulfoxide (DMSO)," Rev Clin Basic Pharm., 5(1-2):I-33 (Jan-Jun. 1985).

U.S. Appl. No. 62/076,854, filed Nov. 7, 2014, Azmi Nasser.

U.S. Appl. No. 62/100,391, filed Jan. 6, 2015, Azmi Nasser.

U.S. Appl. No. 62/112,546, filed Feb. 5, 2015, Azmi Nasser.

U.S. Appl. No. 62/199,778, filed Jul. 31, 2015, Azmi Nasser.

Aird, J., "Controlled Release—SMi Conference," Meeting Report Controlled Release, London, UK, IDrugs 6(4):334-336 (2013).

Amass, L., et al. "A prospective randomized, multicenter acceptability and safety study of direct buprenorphine/naloxone induction in herion-dependent individuals," Addiction 107(1):142-151 (Jan. 2012, e-published Oct. 12, 2011).

Anon (Nov. 30, 2017). "FDA Approves Sublocade™ (Buprenorphine Extended-Release), the First and Only Once-Monthly Injectable Buprenorphine Formulation to Treat Moderate to Severe Opioid Use Disorder," 11 pages (accessed Nov. 29, 2018).

Anon, "Highlights of Prescribing Information Sublocade," 39 pages (Nov. 1, 2017; accessed Nov. 28, 2018).

(56)　　　　　References Cited

OTHER PUBLICATIONS

Astaneh, R., et al., "Changes in morphology of in situ forming PLGA implant prepared by different polymer molecular weight and its effect on release behavior," Journal of Pharmaceutical Sciences, 98(1):135-145 (Jan. 2009).

Aulton's Pharmaceutics: The Design of Manufacture of Medicines, 4th Edition, 2013, Eds. M.E. Aulton et al., Churchill Livingstone, Chapter 22.

Bai-Fang X Sobel et al., "Open-label trial of an injection depot formulation of buprenorphine in opiod detoxification," Drug and Alcohol Dependence, vol. 73, No. 1, Jan. 1, 2004 (Jan. 1, 2004), pp. 11-22, XP055012972.

Baker, D.L., et al., "Gonadotropin-releasing hormone agonist: a new approach to reversible contraception in female deer," Journal of Wildlife Diseases, 40(4):713-724 (Oct. 2004).

Bartsch, W., et al., "Acute Toxicity in Various Solvents in the Mouse and Rat," Arzneimittel-Forschung, Drug Research, 26:1581-1583 (1976).

Basu, S.K., et al., "Protein crystals for the delivery of biopharmaceuticals," Expert Opinion Biological Therapy, 4 (3):301-317 (Mar. 2004).

Becci, P.J., et al., "Subchronic Feeding Study in Beagle Dogs of N-Methylpyrrolidone," Journal of Applied Toxicology, 3(2):83-86 (1983).

Berges, R., et al., "Eligard: Pharmacokinetics, Effect on Testosterone and PSA Levels and Tolerability," European Urology Supplements, 4:20-25 (2005).

Bickel W.K., et al. "Buprenorphine: dose-related blockade of opioid challenge effects in opioid dependent humans," J. Pharmacol Exp. Ther. 1988; 247:47-53.

Bickel, W.K., et al. (1995), "Buprenorphine Treatment of Opioid Dependence: A Review," Experimental and Clinical Psychopharmacology 3(4):477-489.

Boongird, A., et al., "Biocompatibility study of glycofurol in rat brains," Exp. Biol. Med., 236:77-83 (Jan. 2011).

Bowersock, T.L., et al. (1999), "Vaccine delivery to animals," Adv. Drug Deliv. Rev., 38(2):167-194.

Bromberg, L.E., et al., "Sustained release of silver from periodontal wafers for treatment of periodontitis," J. Control Release, 68(1):63-72 (Jul. 31, 2000).

Chandrashekar, B.L., et al., "Sustained Release of Leuprolide Acetate from an In-situ Forming Biodegradable Polytmeric Implant as the Delivery Vehicle," Proceed Int'/Symp Control Re/Bioact Mater., 26:3 (Jul. 1999).

Chen, F.A., et al., "Biodegradable polymer-mediated intratumoral delivery of cisplatin for treatment of human head and neck squamous cell carcinoma in a chimeric mouse model," Head Neck, 25(7):554-560 (Jul. 2003).

Chu, F.M., et al., "A clinical study of 22.5 mg. La-2550: A new subcutaneous depot delivery system for leuprolide acetate for the treatment of prostate cancer," Journal of Urology, 168(3):1199-1203 (Sep. 2002).

Comer, S.D., et al., (Oct. 2005, e-published Sep. 29, 2005). "Buprenorphine/naloxone reduces the reinforcing and subjective effects of heroin in heroin-dependent volunteers," Psychopharmacology 181(4):664-675.

Comers, et al., "Abuse liability of interavenous buprenorphine/naloxone and buprenorphine alone in buprenorphine-maintained intravenous heroin abusers," Addiction, vol. 105, No. 4, pp. 709-718 (2010).

Comers, et al., "Buprenorphine sublingual tablets: effects on IV heroin self-administration by humans," Psychopharmacology, vol. 154, pp. 28-37 (2001).

Contet C., Kieffer BL, Befort K., "Mu opioid receptor: a gateway to drug addiction," Curr Opin Neurobiol 14:370-378, 2004.

Coonts, B.A., et al., (Oct. 1993), "Plasma Concentrations of Naltrexone Base Following Subcutaneous and Intramuscular Injections of Atrigel TM Formulations in Dogs," Pharmaceutical Research: Official Journal of the American Association of Pharmaceutical Scientists PHREEB 7071, 2 pages.

Correia, C.J., et al., "Effects associated with double-blind omission of buprenorphine/naloxone over a 98-h period," Psychopharmacology (Berl). 2006; 189-297-306.

Cox, M.C., et al., (Aug. 2005), "Leuprolide acetate given by a subctaneous extendedrelease injection: less of a pain?," Expen Rev Anticancer Ther 5(4):605-611.

Crawford, E.D., et al., "A 12-month clinical study of LA-2585 (45.0 mg): a new 6-month subcutaneous delivery system for leuprolide acetate for the treatment of prostate cancer," Journal of Urology, 175(2):533-536 (Feb. 2006).

Crist, Richard C., et al., "An Intronic Variant in OPRD1 Predicts Treatment Outcome for Opioid Dependence in African-Americans," Neuropsychopharmacology, 38(10):2003-2010 (Apr. 23, 2013) XP055528570.

Dadey, E.J., (2008), The Atrigel Drug Delivery System, In: Rathbone et al. Eds, Modified-Release Drug Delivery Technology, 2nd Ed., New York, pp. 183-190.

Dernell, W.S., et al., (1998), "Apparent interaction of dimethyl sulfoxide with cisplatin released from polymer delivery devides injected subcutaneously in dogs," J Drug Target 5(5):391-396.

Diagnostic and Statistical Manual of Mental Disorders, 5th Edition DSM-5, American Psychiatric Publishing, pp. 541-546 (2013).

Domb, A.J., et al., "Solid-State and Solution Stability of Poly(anhydrides) and Polyesters," Macromolecules, 22 (5):2117-2122 (1969).

Dunn, R.L., et al., (1996), "Sustained Release of Cisplatin in Dogs from an Injectable Implant Delivery System," Journal of Bioactive and Compatible Polymers, 11:286-300.

Dunn R.S., (2003), "The Atrigel Drug Delivery System," Modified-Release Drug Delivery Technology, Edited by Rathbone, Hadgraft, Roberts, Marcel Dekker, Inc., Chapter 54, pp. 6457-6655.

Duysen, E.G., et al. (1992), "Bioactivity of Polypeptide Growth Factors Released from the Atrigel Drug Delivery System," PHREEB, Abstract No. 2028.

Duysen, E.G., et al., (1993), "Release of Bioactive Growth Factors from the Atrigel Delivery System in Tibial Defect and Dermal Wound Models," PHREE, 10(10):S83, Abstract No. 2043.

Duysen, E.G., et al. (1994), "An Injectable, Biodegradable Delivery System for Antineoplastic Agents," PHREEB, 11 (10):S88, Abstract No. 2071.

Eliaz, R.E., et al., "Delivery of soluble tumor necrosis factor receptor from in-situ forming PLGA implants: in-vivo," Pharm Research, 17(12):1546-1550 (Dec. 2000).

EPO Opposition filed Mar. 30, 2021.

Erickson, N.M., et al., "An invitro degradation study comparing poly(DL-lactide co-glycolide) with acid end groups and ester end groups," 20th Southern Biomedical Engineering Conference (2001).

Evans, H.C., et al., (2004), "Leuprorelin: Subcutaneous Depot Formulation (Eligard) for Advanced Prostate Cancer," Am J. Cancer, 3(3):197-201.

Fareed., A., et al., "Effect of buprenorphine dose on treatment outcome," J. Addict Dis., 31(1):8-18 (2012).

FDA Document K982865 (1998), Atrix Laboratories, Inc. 13 pages.

FDA Document K994137 (2000), Atrix Laboratories, Inc. 9 pages.

Frank, K.R., et al., "Controlled Release of Bioactive Growth Factors from a Biodegradable Deliver System," PHREEB, 11(10):S88, Abstract No. 2070 (1994).

Frost, J.J., Wagner, H.N. Jr., Dannals, R.F., Ravert, H.T., Links, J.M. Wilson, A.A., Burns, H.D., Wong, D.F., McPherson, R.W., Rosenbaum, A.E., Kuhar, M.d. & Snyder, S.H. (1985), "Imaging opiate receptors in the human brain by positron tomography," Comp. Assist Tomogr., 9:231-236.

Fudala, P.J., et al., (Sep. 4, 2003), "Office-based treatment of opiate addiction with a sublingual-tablet formulation of buprenorphine and naloxone," N. Engl. J. Med. 349(10):949-958.

Gerentes, P., et al., (2002), "Study of a chitin-based gel as injectable material in periodontal surgery," Biomaterials 23 (5): 1295-1302.

Gerstein, D.R., et al., (Sep. 20, 1990), "Treating drug problems," N. Engl. J. Med., 323(12):844-848.

T0239/16-3.3.01—EPO Opposition Decision of Sep. 13, 2017 for EP1591122.

Tipton, A.J., et al., "A Biodegradable, Injectable Delivery System for Non-Steroidal Anti-Flammatory Drugs," Pharmaceutical Research, 8(10), PDD 7279, 2 pages (Oct. 1991).

(56) References Cited

OTHER PUBLICATIONS

Titeler, M., Lyon, R.A., Kuhar, M.J., Frost, J.J., Dannals, R.F., Leonhardt, S., Bullock, A., Rydelek, L. T., Price, D.L. & Struble, R.G., (1989), "Mu opiate receptors are selectively labeled by [3H]-carfentanil in human and rat brain," Eur J Pharmacol, 167, 221-228.

Tkacz, J., et al., (Jan-Feb. 2012, e-published Nov. 18, 2011), "Compliance with buprenorphine medication-assisted treatment and relapse to opioid use," Am J Addict, 21(1):55-62.

Tserki, V., et al., (Feb. 2006), "Biodegradable aliphatic polyesters. Part II, Synthesis and characterization of chain extended poly(butylene succinate-co-butylene adipate)," Polymer Degradation and Stability 91(2):377-384.

Tunn, U.W., "A 6-month depot formulation of leuprolide acetate is safe and effective in daily clinical practice: a non-in terventional prospective study in 1273 patents," BMC Urology, 11:15 (Jul. 29, 2011).

Vahia, V.N., et al., "Diagnostic and statistical manual of mental disorders 5: A quick glance," Indian J. Psychiatry, 55 (3):220-223 (2013).

Van Ameijden, E.J., et al., "Dose-effect relationship between overdose mortality and prescribed methadone dosage in low-threshold maintenance programs," Addict Behav, 24(4):559-563 (Jul.-Aug. 1999).

Veilleux, J.C., Colvin P.J., Anderson J., York C., Heinz, A.J., "A review of opioid dependence treatment: pharmacological and psychosocial interventions to treat opioid addiction," Clin Psycho/Rev 2010; 30:155-166.

Walsh, S.L., et al., "Acute administration of buprenorphine in humans: partial agonist and blockade effects," J. Pharmacol. Exp. Ther., 1995; 274:36-372.

Walsh, S.L. et al., "Clinical pharmacology of buprenorphine: ceiling effects at high doses," Clin Pharm Ther 1994; 55:569-580.

Wang, L., et al., "Structure formation in injectable poly(lactide-co-glycolide) depots," J Control Release, 90(3):345-354 (Jul. 31, 2003).

Wang, L., et al., "Drug release from injectable depots: two different in vitro mechanisms," J Control Release, 99 (2):207-216 (Sep. 30, 2004).

Wiens, B.L., et al. (Nov. 2013), "Missing Data in Noninferiority Trials," Stat Biopharm, 5(4):383-393.

Winzenberg, G., et al., "Biodegradable polymers and their potential use in parenteral veterinary drug delivery systems," Adv Drug Deliv Rev., 56(10):1453-1466 (Jun. 23, 2004).

Wolff, E.D., et al. (1994), "Use of Bio-Beads SM-4 Adsorbent for Bioburden Testing of Atrigel TM Biodegradable Delivery System Containing 10% Doxycycline," ASM Las Vegas 1994, Abstracts, 3 pages.

World Health Organization (2001), N-Methyl-2-Pyrrolidone, Concise International Chemical Assessment Document 35, 39 pages.

Written Opinion mailed on Dec. 12, 2018, for PCT Application No. PCT/IB2018/000770, filed Jun. 15, 2018, 9 pages.

Written Opinion mailed on Jun. 11, 2015, for PCT Application No. PCT/GB2015/050676, filed on Mar. 9, 2015, 6 pages.

Written Opinion mailed on Mar. 24, 2016 for PCT Application No. PCT/IP2015/002269, filed on Nov. 6, 2015, 10 pages.

Wroblewski, F., et al., "The clinical significance of alterations in transaminase activities of serum and other body fluids," Adv. Clin. Chem., 1(2):313-351 (1958).

Xia, Y., et al., (Jul. 18, 2002), "Uniform biodegradable microparticle systems for controlled release," J Control Release, 82(1):137-147.

Zhu, G., et al., "Stabilization of proteins encapsulated in cylindrical poly(lactide-coglycolide) implants: mechanism of stabilization by basic additives," PHarm Res., 17(3):351-357 (2000).

Zubieta, J-K et al., (Sep. 2000), "Buprenorphine-induced changes in mu-opioid receptor availability in male herion-dependent volunteers: a preliminary study," Neuropsychopharmacology 23(3):326-334.

* cited by examiner

BUPRENORPHINE DOSING REGIMENS

CROSS-REFERENCES TO RELATED APPLICATIONS

This application is a continuation of U.S. application Ser. No. 17/985,253 filed Nov. 11, 2022, which is a continuation of U.S. application Ser. No. 17/217,914 filed Mar. 30, 2021, now U.S. Pat. No. 11,839,611, which is a continuation of U.S. application Ser. No. 15/523,986, a National Stage of PCT/IB2015/002269 filed Nov. 6, 2015, now U.S. Pat. No. 11,000,520, which claims priority to U.S. Application No. 62/076,854 filed Nov. 7, 2014, U.S. Application No. 62/100, 391 filed Jan. 6, 2015; U.S. Application No. 62/112,546 filed Feb. 5, 2015, and U.S. Application No. 62/199,778 filed Jul. 31, 2015, the disclosures of all of which are incorporated by reference herein in their entirety.

BACKGROUND

The disclosure is directed to dosing regimens for sustained-release buprenorphine formulations that provide sustained therapeutic levels of buprenorphine and μ-opioid receptor occupancy for the treatment of pain and opioid use disorders.

Opioid addiction is a neurobehavioral syndrome characterized by the repeated, compulsive seeking and use of an opioid despite adverse social, psychological, and/or physical consequences. Opioid addiction is a problem with high costs to individuals, families, and society. The use of prescription opioids has tremendously increased in the past decade in the United States (from 174 million in 2000 to 257 million in 2009) due to the widespread availability and variety of prescription opioid products, and changes in treatment paradigms. Opioid abuse, addiction, overdose, and other health and social consequences of opioid misuse are taking a rapidly growing toll on individuals and institutions in the United States. It is estimated that 2.2 to 2.4 million individuals initiate non-medical use of opioids in the United States each year and non-medical opioid use now exceeds use of many conventional street drugs, including cocaine and heroin. Overdose deaths from prescription drugs have exceeded those from street drugs since 2002 and have surpassed traffic accidents as a cause of accidental death. In 2011, over 1,252,500 of 2.5 million emergency department (ED) visits associated with drug abuse or addiction involved illicit drugs, including 258,482 ED visits related to heroin and about 420,040 ED visits related to narcotic pain relievers.

Opioid receptors are located in both the central nervous system (CNS) and the periphery. In the CNS, they are found in high concentrations in the limbic system and the spinal cord. The natural ligands for the opioid receptors are a group of neuropeptides known as endorphins. Opioid analgesics mimic the action of these natural ligands, but have a more prolonged action as they are not subject to rapid local metabolism. Three major opioid receptor subclasses have been identified: μ-, κ-, and δ-. Buprenorphine is a partial opioid agonist at the μ-opioid receptor, with antagonist properties at the κ-receptor. In contrast to a full agonist, buprenorphine at the μ-receptor has less maximal euphoric effect, and a ceiling on its respiratory depressant effects. By binding to μ-opioid receptors in the brain, buprenorphine reduces craving for opioids and opiate withdrawal symptoms, minimizing the need of opioid-dependent patients to use illicit opiate drugs. For the maintenance treatment of opioid dependence, SUBUTEX® (buprenorphine; Indivior PLC), SUBOXONE® tablets (buprenorphine/naloxone; Indivior PLC), or SUBOXONE® film (buprenorphine/naloxone; Indivior PLC) may be given as a single daily dose ranging from 4 to 24 mg per day, with the recommended dosage being 16 mg buprenorphine per day.

A major issue in the pharmacological treatment of opioid dependence is the high rate of non-adherence. Currently, there is no approved parenterally-administered, sustained-release buprenorphine product indicated for the treatment of opioid dependence. Such a product could offer advantages over existing buprenorphine pharmacotherapy by improving patient compliance and reducing diversion, abuse, and unintended exposure, particularly regarding children.

To this end, the present disclosure is directed to dosing regimens for sustained-release formulations of buprenorphine that provide, among other benefits, optimal buprenorphine dosages, therapeutic buprenorphine concentrations, and therapeutic μ-opioid receptor occupancy for the treatment of opioid dependence or pain.

SUMMARY

The disclosure provides dosing regimens for treating opioid dependence or pain in a human in need thereof including the steps of: (a) administering a first composition including a dose of buprenorphine to the human once per month by injection for one month, two months, or three months; and thereafter (b) administering a second composition including a dose of buprenorphine to the human once per month by injection beginning with the second month, third month, or fourth month of administration, respectively, and for each month thereafter; to treat the opioid dependence or pain; wherein the amount of buprenorphine in the first composition is greater than the amount of buprenorphine in the second composition. In embodiments, the dosing regimen is for treating opioid dependence. In embodiments, the dosing regimen is for treating pain.

A comprehensive model-based approach was developed to describe the population pharmacokinetics of sustained-release buprenorphine formulations in opioid-dependent subjects and to define the relationships between buprenorphine plasma concentrations with μ-opioid receptor occupancy (μORO) and clinical efficacy. The results of these analyses provide new insight into the long-acting pharmacokinetic and pharmacokinetic/μORO profile of sustained-release buprenorphine formulations. These findings indicated that sustained-release buprenorphine formulations can become an effective treatment of opioid dependence by addressing the compliance, reducing diversion, abuse, and unintended exposure associated with conventional treatments. The disclosure empirically combined clinical molecular neuroimaging, and plasma concentration and pharmacodynamic data to predict an effective dosing regimens for sustained-release buprenorphine formulations.

The disclosure provides a methodological approach to exploit all the information available, using comprehensive modeling approach to integrate and learn from the data generated in different studies the pharmacokinetic and PK/PD characteristics of sustained-release buprenorphine formulations. This learning has been subsequently applied to address relevant questions for the clinical development of sustained-release buprenorphine formulations.

This strategy was implemented by initially defining a population pharmacokinetic model of buprenorphine and norbuprenorphine using data obtained in 36 opioid-dependent subjects who received Formulation D (as described herein) with 50 mg, 100 mg, or 200 mg of buprenorphine base. A population pharmacokinetic/μORO model was developed using data (buprenorphine pharmacokinetic and μORO) collected in 15 heroin-dependent subjects (5 receiving buprenorphine daily tablet doses of 32 mg, 16 mg, 2 mg, or placebo and 10 receiving buprenorphine daily tablet dose of 16 mg). The results of the buprenorphine population pharmacokinetic analysis were combined with results of the population pharmacokinetic/μORO analysis to estimate the expected μORO after repeated subcutaneous injections of different doses of Formulation D administered once a month. As expected, blockade of hydromorphone agonist effects, withdrawal symptoms and plasma buprenorphine concentrations were correlated with μORO.

Norbuprenorphine is a major metabolite of buprenorphine and potent agonist of μ, δ, and κ opioid receptors. However, while norbuprenorphine is able to bind the μ-opioid receptors, it does not appreciable distribute to the CNS and would not affect the pharmacodynamic endpoints. The reasons why norbuprenorphine was included in the model is that it binds to peripheral μ-opioid receptors, with potential involvement in safety, and is important to the overall clinical development plan. In any case, considering that the norbuprenorphine concentrations were available, it was a reasonable strategy to evaluate these data in a comprehensive model for a better characterization and understanding of buprenorphine pharmacokinetics.

Analysis of the pharmacokinetic profile of Formulation D revealed a complex absorption profile, presenting double peaks and a prolonged plasma terminal half-life. These distinguishing features of the pharmacokinetics of Formulation D required the development of a complex pharmacokinetic model accounting for these dual absorption processes: a first absorption process that was associated with an initial rapid delivery from the subcutaneous injection site, and a second absorption process that was associated with a slow release from the sustained-release formulation into the systemic circulation. The mean transit time associated with the slow release from the sustained-release formulations could be estimated at 10 weeks, which is the likely reason for the curvilinear shape of the plasma concentration-time profile.

The buprenorphine plasma exposure increased proportionally with dose. The established model was stable and described the data well. The covariate analysis was unable to detect any relevant impact of the demographic characteristics of the subjects enrolled in the trial, probably due to the limited sample size.

The clinical efficacy of opioid medication assisted therapy for the treatment of opioid dependence is believed to result from a medication's ability to alleviate withdrawal symptoms, and bind μ-opioid receptors resulting in blockade of subjective agonist effects. Greenwald et al, Biol Psychiatry, 61:101-110 (2007) suggests that the threshold for suppressing withdrawal and the blockade of agonist symptom effects is between 50-60% buprenorphine μORO while additional benefit and clinical efficacy was observed at 70% μORO. As a result from these findings, dose selection criterion was based on the selection of a dose appropriate to reaching and maintaining a ORO greater than 70% after multiple doses.

The population pharmacokinetic/u ORO model fully characterized the relationship between buprenorphine plasma levels and μORO. The relationship between buprenorphine plasma concentration and μORO was best described by an $E_{max}$ model with $EC_{50}$ of 0.67 ng/ml and $E_{max}$ of 91%. The $E_{max}$ model showed a linear relationship between μORO up to the desired 70% receptor occupancy and buprenorphine concentrations up to about 2 ng/ml. At buprenorphine concentrations greater than 2 ng/mL, saturation occurred on μORO where 4.5-fold increase in observed buprenorphine concentrations resulted in observed μORO between 70% and less than 90%. Thus, once μORO is saturated, increasing doses are not expected to exert any appreciable effect. A linear correlation was established between buprenorphine clinical efficacy (withdrawal suppression and blockade of hydromorphone agonist subjective effects) and μORO. Trial simulation indicated that ≥70% receptor occupancy may be achieved after multiple doses of 200 mg Formulation D once every 28 days.

DETAILED DESCRIPTION

In one embodiment, the disclosure provides methods of treating opioid dependence or pain in a human in need thereof comprising the steps of (a) administering a first composition comprising a dose of buprenorphine to the human once per month by injection for one month; and thereafter (b) administering a second composition comprising a dose of buprenorphine to the human once per month by injection beginning with the second month of administration and for each month thereafter; to treat the opioid dependence or pain; wherein the amount of buprenorphine in the first composition is greater than the amount of buprenorphine in the second composition.

In one embodiment, the disclosure provides methods of treating opioid dependence or pain in a human in need thereof comprising the steps of (a) administering a first composition comprising a dose of buprenorphine to the human once per month by injection for two months; and thereafter (b) administering a second composition comprising a dose of buprenorphine to the human once per month by injection beginning with the third month of administration and for each month thereafter; to treat the opioid dependence or pain; wherein the amount of buprenorphine in the first composition is greater than the amount of buprenorphine in the second composition.

In one embodiment, the disclosure provides methods of treating opioid dependence or pain in a human in need thereof comprising the steps of (a) administering a first composition comprising a dose of buprenorphine to the human once per month by injection for three months; and thereafter (b) administering a second composition comprising a dose of buprenorphine to the human once per month by injection beginning with the fourth month of administration and for each month thereafter; to treat the opioid dependence or pain; wherein the amount of buprenorphine in the first composition is greater than the amount of buprenorphine in the second composition.

As discussed herein, the amount of buprenorphine in the first composition is greater than the amount of buprenorphine in the second composition, where the second composition is administered as a maintenance therapy. Without intending to be bound by any theory, it has been discovered that the first composition of buprenorphine administered once monthly for 1 to 3 months produces therapeutically effective levels of buprenorphine and a sufficient μ-opioid receptor occupancy to suppress opioid withdrawal signs and symptoms and block responses to a μ-opioid receptor agonist. Treatment for 1 to 3 months at the higher dose of buprenorphine allows the patients to have reduced cravings, physically and/or psychologically, for opioids. It has also been unexpectedly discovered that once the patient has achieved the therapeutically effective levels of buprenorphine and μ-opioid receptor occupancy, including the reduced cravings for opioids, the second composition comprising a lower dose of buprenorphine can be safely and effectively administered once monthly to the human to maintain the therapeutically effective treatment, without the lower dosage causing a relapse of opioid abuse by the patients. Advantages of administering the lower dosage include decreased side effects, and a step-wise approach to reducing the dosage to completely taper off treatment.

The term "buprenorphine" refers to buprenorphine in the form of a free base and buprenorphine in the form of a pharmaceutically acceptable salt. In the formulations described herein, buprenorphine is preferably in the form of a free base.

The term "sustained-release buprenorphine formulation" refers to any formulation comprising buprenorphine that can be administered by injection and that can provide therapeutic levels of buprenorphine for at least 1 month. The injection can be a subcutaneous injection. In other embodiments, the injection can be an intramuscular injection.

The "therapeutic levels" of buprenorphine provided by the sustained-release buprenorphine formulations are at therapeutic levels that are effective: (a) in the treatment of opioid use disorders, such as opioid dependence; (b) in suppressing opioid withdrawal signs and symptoms; and (c) in treating pain. Therapeutic levels can be measured by the buprenorphine concentration ($C_{ave}$) in the human and/or the μ-opioid receptor occupancy in the patient, each of which are described herein.

The term "one month" means 28 days to 31 days. In one embodiment, one month is 28 days. In one embodiment, one month is 30 days. In one embodiment, one month is 31 days.

"Opioid use disorder" is defined in the *Diagnostic and Statistical Manual for Mental Disorders, 5th Edition (DSM-5)* as a problematic pattern of opioid use leading to clinically significant impairment or distress, as manifested by symptoms described in the DSM-5. As used herein, the term "opioid use disorder" is synonymous with "opioid dependence," "opioid addiction," and "opioid abuse."

The term "opioid withdrawal signs and symptoms" includes one or more signs and symptoms associated with withdrawal from opioids. Such signs and symptoms can include one or more of the following: agitation, anxiety, muscle aches, increased tearing, insomnia, runny nose, sweating, yawning, abdominal cramping, diarrhea, dilated pupils, goose bumps, nausea, and vomiting. Opioid withdrawal symptoms can begin to occur from a few hours to a few days after the last intake of an opioid, with the time being dependent on the opioid, the person's metabolism, and other factors.

In one embodiment, the sustained-release buprenorphine formulation is a formulation described in U.S. Pat. No. 8,921,387 or U.S. Pat. No. 8,975,270, the disclosures of which are incorporated by reference herein in their entirety. In one embodiment, the sustained-release buprenorphine formulation is a formulation described in US Publication No. 2013/210853, the disclosures of which are incorporated by reference herein in their entirety. In one embodiment, the sustained-release buprenorphine formulation is a formulation described in US Publication No. 2013/0202658, the disclosure of which is incorporated by reference herein in its entirety. In one embodiment, the sustained-release buprenorphine formulation is a formulation described in U.S. Pat. No. 8,236,755, the disclosure of which is incorporated by reference herein in its entirety. In one embodiment, the sustained-release buprenorphine formulation is a formulation described in WO 2014/016428, the disclosure of which is incorporated by reference herein in its entirety.

In one embodiment, the sustained-release buprenorphine formulation is Formulation D. "Formulation D" is a flowable composition that comprises, consists essentially of, or consists of: (i) about 18 wt % buprenorphine in the form of the free base; (ii) about 32 wt % of a 50:50 poly(DL-lactide-co-glycolide) copolymer having a carboxy terminal group and having an average molecular weight of about 9,000 Daltons to about 19,000 Daltons; and (iii) about 50 wt % of N-methyl-2-pyrrolidone.

In one embodiment, the sustained-release buprenorphine formulation is Formulation C. "Formulation C" is a flowable composition that comprises, consists essentially of, or consists of: (i) about 14 wt % to about 22 wt % buprenorphine in the form of the free base; (ii) about 22 wt % to about 42 wt % of a 50:50 to 80:20 poly(DL-lactide-co-glycolide) copolymer having an average molecular weight of about 5,000 Daltons to about 30,000 Daltons; and (iii) about 40 wt % to about 60 wt % of N-methyl-2-pyrrolidone.

In one embodiment, the sustained-release buprenorphine formulation is Formulation B. "Formulation B" is a flowable composition that comprises, consists essentially of, or consists of: (i) about 10 wt % to about 30 wt % buprenorphine in the form of the free base; (ii) about 10 wt % to about 60 wt % of a 50:50 to 95:5 poly(DL-lactide-co-glycolide) copolymer having an average molecular weight of about 5,000 Daltons to about 40,000 Daltons; and (iii) about 30 wt % to about 70 wt % of N-methyl-2-pyrrolidone.

In one embodiment, the sustained-release buprenorphine formulation is Formulation A. "Formulation A" is a flowable composition that comprises, consists essentially of, or consists of: (i) at least one biodegradable thermoplastic polymer; (ii) at least one organic liquid which comprises an amide, an ester, a carbonate, a ketone, a lactam, an ether, a sulfonyl, or a combination thereof; and (iii) about 5 wt % to about 30 wt % of buprenorphine in the form of a free base or pharmaceutically acceptable salt. In one embodiment, the buprenorphine is in the form of a free base. In other embodiments, the buprenorphine is present in an amount from about 10 wt % to about 25 wt %; or in an amount from about 15 wt % to about 20 wt %. In other embodiments, the organic liquid is present in an amount of about 30 wt % to about 70 wt %; or in an amount of about 40 wt % to about 60 wt %. In one embodiment, the organic liquid is N-methyl-2-pyrrolidone, 2-pyrrolidone, propylene glycol, polyethylene glycol, ethanol, acetone, tetrahydrofurfuryl alcohol, dimethyl isosorbide, acetic acid, lactic acid, methyl lactate, ethyl lactate, monomethyl succinate acid, monomethyl citric acid, glycofurol, glycerol formal, isopropylidene glycol, 2,2-dimethyl-1,3-dioxolone-4-methanol, dimethylformamide, dimethylacetamide, N,N-dimethylformamide, propylene carbonate, triacetin, dimethylsulfoxide, dimethylsulfone, epsilon-caprolactone, butyrolactone, caprolactam, and a mixture of two or more thereof. In other embodiments, the organic liquid is N-methyl-2-pyrrolidone, 2-pyrrolidone, N,N-dimethylformamide, dimethyl sulfoxide, propylene carbonate, caprolactam, polyethylene glycol, ethanol, or a mixture of two or more thereof. In other embodiments, the organic liquid is N-methyl-2-pyrrolidone. In other embodiments, the biodegradable thermoplastic polymer is present in an amount of about 10 wt % to about 60 wt %; or in an amount of about 20 wt % to about 40 wt %. In one embodiment, the polymer is a polylactide, a polyglycolide, a polycaprolactone, a copolymer thereof, a terpolymer thereof, any combination thereof, or a mixture of two or more thereof. In one embodiment, the polymer is a poly(DL-lactide-co-glycolide) copolymer. The polymer, such as the poly(DL-lactide-co-glycolide) copolymer, can have an average molecular weight of about 1,000 Daltons to about 50,000 Daltons; or from about 5,000 Daltons to about 40,000 Daltons; or from about 5,000 Daltons to about 30,000 Daltons; or from about 5,000 Daltons to about 20,000 Daltons; or from about 10,000 Daltons to about 20,000 Daltons. The poly(DL-lactide-co-glycolide) copolymer can be a 50:50 to 95:5 poly(DL-lactide-co-glycolide) copolymer; or a 50:50 to 80:20 poly(DL-lactide-co-glycolide) copolymer; or a 50:50 poly(DL-lactide-co-glycolide) copolymer.

The phrase "average molecular weight" refers to the weight average molecular weight of a polymer as determined by gel permeation chromatography (also known as GPC or size exclusion chromatography (SEC)) using tetrahydrofuran (THF) as the solvent and using a molecular weight calibration curve using polystyrene standards.

In one embodiment of the methods described herein, the first composition comprises from about 25 mg to about 500 mg buprenorphine, and the second composition comprises from about 1 mg to about 400 mg buprenorphine; provided that the amount of buprenorphine in the first composition is greater than the amount of buprenorphine in the second composition. In another embodiment, the first composition comprises from about 150 mg to about 500 mg buprenorphine, and the second composition comprises from about 10 mg to about 250 mg buprenorphine; provided that the amount of buprenorphine in the first composition is greater than the amount of buprenorphine in the second composition. In another embodiment, the first composition comprises from 176 mg to about 500 mg buprenorphine, and the second composition comprises from about 10 mg to 175 mg buprenorphine. In another embodiment, the first composition comprises from about 200 mg to about 400 mg buprenorphine, and the second composition comprises from about 25 mg to about 160 mg buprenorphine. In another embodiment, the first composition comprises from about 250 mg to about 350 mg buprenorphine, and the second composition comprises from about 50 mg to about 150 mg buprenorphine. In another embodiment, the first composition comprises from about 280 mg to about 320 mg buprenorphine, and the second composition comprises from about 80 mg to about 120 mg buprenorphine. In another embodiment, the first composition comprises about 300 mg buprenorphine, and the second composition comprises about 100 mg buprenorphine.

The therapeutically effective buprenorphine concentration produced by the methods described herein is an average buprenorphine concentration ($C_{ave}$) of about 0.5 ng/mL to about 5 ng/mL in the human. In one embodiment, average buprenorphine concentration ($C_{ave}$) is from about 1 ng/mL to about 4.5 ng/mL in the human. In one embodiment, average buprenorphine concentration ($C_{ave}$) is from about 1.5 ng/ml to about 4 ng/mL in the human. In one embodiment, average buprenorphine concentration ($C_{ave}$) is from about 1.5 ng/ml to about 3.5 ng/mL in the human. In one embodiment, average buprenorphine concentration ($C_{ave}$) is from about 2 ng/ml to about 4 ng/mL in the human. In one embodiment, average buprenorphine concentration ($C_{ave}$) is from about 2 ng/mL to about 3 ng/mL in the human. In one embodiment, average buprenorphine concentration ($C_{ave}$) is from about 2.5 ng/mL to about 3.5 ng/mL in the human. In one embodiment, average buprenorphine concentration ($C_{ave}$) is from about 3 ng/ml to about 4 ng/mL in the human. In one embodiment, average buprenorphine concentration ($C_{ave}$) is from about 1.8 ng/mL to about 3.7 ng/mL in the human. In the methods described herein, the average buprenorphine concentration is achieved from one to four months after the first injection, when the injections are given on a monthly basis. In one embodiment, the average buprenorphine concentration is achieved from one to three months after the first injection, when the injections are given on a monthly basis. In one embodiment, the average buprenorphine concentration is achieved from one to two months after the first injection, when the injections are given on a monthly basis. In one embodiment, the average buprenorphine concentration is achieved within two months after the first injection, when the injections are given on a monthly basis. In one embodiment, the average buprenorphine concentration is achieved within one month after the first injection.

The dosing regimen used in the methods described herein produces a μ-opioid receptor occupancy, as measured by the maximum effect model of Equation 1 (described herein), greater than 60% in the human being treated. In one embodiment, the methods produce a μ-opioid receptor occupancy (as measured by a maximum effect model of Equation 1) of at least 70%. In one embodiment, the methods produce a μ-opioid receptor occupancy (as measured by a maximum effect model of Equation 1) of greater than 60% to about 90%. In one embodiment, the methods produce a μ-opioid receptor occupancy (as measured by a maximum effect model of Equation 1) of about 65% to about 85%. In one embodiment, the methods produce a μ-opioid receptor occupancy (as measured by a maximum effect model of Equation 1) of about 65% to about 80%. In one embodiment, the methods produce a μ-opioid receptor occupancy (as measured by a maximum effect model of Equation 1) of about 65% to about 76%. In one embodiment, the methods produce a μ-opioid receptor occupancy (as measured by a maximum effect model of Equation 1) of about 65% to about 75%. In the methods described herein, the μ-opioid receptor occupancy is achieved from one to four months after the first injection, when the injections are given on a monthly basis. In one embodiment, the μ-opioid receptor occupancy is achieved from one to three months after the first injection, when the injections are given on a monthly basis. In one embodiment, the μ-opioid receptor occupancy is achieved from one to two months after the first injection, when the injections are given on a monthly basis. In one embodiment, the μ-opioid receptor occupancy is achieved within two months after the first injection, when the injections are given on a monthly basis. In one embodiment, the μ-opioid receptor occupancy is achieved within one month after the first injection, when the injections are given on a monthly basis.

In one embodiment, the disclosure provides methods of treating opioid dependence or pain in a human in need thereof comprising the steps of (a) administering a first composition of Formulation A, B, C, or D comprising buprenorphine to the human once per month by injection for one month; and thereafter (b) administering a second composition of Formulation A, B, C, or D comprising buprenorphine to the human once per month by injection beginning with the second month of administration and for each month thereafter; to treat the opioid dependence or pain; wherein the amount of buprenorphine in the first composition is greater than the amount of buprenorphine in the second composition. In one embodiment, the first and second compositions are Formulation A. In one embodiment, the first and second compositions are Formulation B. In one embodiment, the first and second compositions are Formulation C. In one embodiment, the first and second compositions are Formulation D. In one embodiment, the first composition comprises from about 25 mg to about 500 mg buprenorphine, and the second composition comprises from about 1 mg to about 400 mg buprenorphine; provided that the amount of buprenorphine in the first composition is greater than the amount of buprenorphine in the second composition. In another embodiment, the first composition comprises from about 150 mg to about 500 mg buprenorphine, and the second composition comprises from about 10 mg to about 250 mg buprenorphine; provided that the amount of buprenorphine in the first composition is greater than the amount of buprenorphine in the second composition. In another embodiment, the first composition comprises from 176 mg to about 500 mg buprenorphine, and the second composition comprises from about 10 mg to 175 mg buprenorphine. In another embodiment, the first composition comprises from about 200 mg to about 400 mg buprenorphine, and the second composition comprises from about 25 mg to about 160 mg buprenorphine. In another embodiment, the first composition comprises from about 250 mg to about 350 mg buprenorphine, and the second composition comprises from about 50 mg to about 150 mg buprenorphine. In another embodiment, the first composition comprises from about 280 mg to about 320 mg buprenorphine, and the second composition comprises from about 80 mg to about 120 mg buprenorphine. In another embodiment, the first composition comprises about 300 mg buprenorphine, and the second composition comprises about 100 mg buprenorphine. In one embodiment, one month is 28 days. In one embodiment, one month is 30 days. In one embodiment, one month is 31 days. In one embodiment, the injection is a subcutaneous injection.

In one embodiment, the disclosure provides methods of treating opioid dependence or pain in a human in need thereof comprising the steps of (a) administering a first composition of Formulation A, B, C, or D comprising buprenorphine to the human once per month by injection for two months; and thereafter (b) administering a second composition of Formulation A, B, C, or D comprising buprenorphine to the human once per month by injection beginning with the third month of administration and for each month thereafter; to treat the opioid dependence or pain; wherein the amount of buprenorphine in the first composition is greater than the amount of buprenorphine in the second composition. In one embodiment, the first and second compositions are Formulation D. In one embodiment, the first composition comprises from about 25 mg to about 500 mg buprenorphine, and the second composition comprises from about 1 mg to about 400 mg buprenorphine; provided that the amount of buprenorphine in the first composition is greater than the amount of buprenorphine in the second composition. In another embodiment, the first composition comprises from about 150 mg to about 500 mg buprenorphine, and the second composition comprises from about 10 mg to about 250 mg buprenorphine; provided that the amount of buprenorphine in the first composition is greater than the amount of buprenorphine in the second composition. In another embodiment, the first composition comprises from 176 mg to about 500 mg buprenorphine, and the second composition comprises from about 10 mg to 175 mg buprenorphine. In another embodiment, the first composition comprises from about 200 mg to about 400 mg buprenorphine, and the second composition comprises from about 25 mg to about 160 mg buprenorphine. In another embodiment, the first composition comprises from about 250 mg to about 350 mg buprenorphine, and the second composition comprises from about 50 mg to about 150 mg buprenorphine. In another embodiment, the first composition comprises from about 280 mg to about 320 mg buprenorphine, and the second composition comprises from about 80 mg to about 120 mg buprenorphine. In another embodiment, the first composition comprises about 300 mg buprenorphine, and the second composition comprises about 100 mg buprenorphine. In one embodiment, one month is 28 days. In one embodiment, one month is 30 days. In one embodiment, one month is 31 days. In one embodiment, the injection is a subcutaneous injection.

In one embodiment, the disclosure provides methods of treating opioid dependence or pain in a human in need thereof comprising the steps of (a) administering a first composition of Formulation A, B, C, or D comprising buprenorphine to the human once per month by injection for three months; and thereafter (b) administering a second composition of Formulation A, B, C, or D comprising buprenorphine to the human once per month by injection beginning with the fourth month of administration and for each month thereafter; to treat the opioid dependence or pain; wherein the amount of buprenorphine in the first composition is greater than the amount of buprenorphine in the second composition. In one embodiment, the first and second compositions are Formulation D. In one embodiment, the first composition comprises from about 25 mg to about 500 mg buprenorphine, and the second composition comprises from about 1 mg to about 400 mg buprenorphine; provided that the amount of buprenorphine in the first composition is greater than the amount of buprenorphine in the second composition. In another embodiment, the first composition comprises from about 150 mg to about 500 mg buprenorphine, and the second composition comprises from about 10 mg to about 250 mg buprenorphine; provided that the amount of buprenorphine in the first composition is greater than the amount of buprenorphine in the second composition. In another embodiment, the first composition comprises from 176 mg to about 500 mg buprenorphine, and the second composition comprises from about 10 mg to 175 mg buprenorphine. In another embodiment, the first composition comprises from about 200 mg to about 400 mg buprenorphine, and the second composition comprises from about 25 mg to about 160 mg buprenorphine. In another embodiment, the first composition comprises from about 250 mg to about 350 mg buprenorphine, and the second composition comprises from about 50 mg to about 150 mg buprenorphine. In another embodiment, the first composition comprises from about 280 mg to about 320 mg buprenorphine, and the second composition comprises from about 80 mg to about 120 mg buprenorphine. In another embodiment, the first composition comprises about 300 mg buprenorphine, and the second composition comprises about 100 mg buprenorphine. In one embodiment, one month is 28 days. In one embodiment, one month is 30 days. In one embodiment, one month is 31 days. In one embodiment, the injection is a subcutaneous injection.

In one embodiment, the disclosure provides methods of treating opioid dependence or pain in a human in need thereof comprising the steps of (a) administering a first composition of Formulation A, B, C, or D comprising buprenorphine to the human once per month by injection for four months; and thereafter (b) administering a second composition of Formulation A, B, C, or D comprising buprenorphine to the human once per month by injection beginning with the fifth month of administration and for each month thereafter; to treat the opioid dependence or pain; wherein the amount of buprenorphine in the first composition is greater than the amount of buprenorphine in the second composition. In one embodiment, the first and second compositions are Formulation D. In one embodiment, the first composition comprises from about 25 mg to about 500 mg buprenorphine, and the second composition comprises from about 1 mg to about 400 mg buprenorphine; provided that the amount of buprenorphine in the first composition is greater than the amount of buprenorphine in the second composition. In another embodiment, the first composition comprises from about 150 mg to about 500 mg buprenorphine, and the second composition comprises from about 10 mg to about 250 mg buprenorphine; provided that the amount of buprenorphine in the first composition is greater than the amount of buprenorphine in the second composition. In another embodiment, the first composition comprises from 176 mg to about 500 mg buprenorphine, and the second composition comprises from about 10 mg to 175 mg buprenorphine. In another embodiment, the first composition comprises from about 200 mg to about 400 mg buprenorphine, and the second composition comprises from about 25 mg to about 160 mg buprenorphine. In another embodiment, the first composition comprises from about 250 mg to about 350 mg buprenorphine, and the second composition comprises from about 50 mg to about 150 mg buprenorphine. In another embodiment, the first composition comprises from about 280 mg to about 320 mg buprenorphine, and the second composition comprises from about 80 mg to about 120 mg buprenorphine. In another embodiment, the first composition comprises about 300 mg buprenorphine, and the second composition comprises about 100 mg buprenorphine. In one embodiment, one month is 28 days. In one embodiment, one month is 30 days. In one embodiment, one month is 31 days. In one embodiment, the injection is a subcutaneous injection.

The disclosure provides dosing regimens for treating opioid dependence or pain in a human in need thereof including the steps of: (a) administering a first composition including a dose of buprenorphine to the human once per month by injection for one month, two months, or three months; and thereafter (b) administering a second composition including a dose of buprenorphine to the human once per month by injection beginning with the second month, third month, or fourth month of administration, respectively, and for each month thereafter; to treat the opioid dependence or pain; wherein the amount of buprenorphine in the first composition is greater than the amount of buprenorphine in the second composition. In embodiments, the dosing regimen is for treating opioid dependence. In embodiments, the dosing regimen is for treating pain. In embodiments, the first and second compositions comprise (i) buprenorphine in the form of a free base or a pharmaceutically acceptable salt; (ii) ethanol or N-methyl-2-pyrrolidone; (iii) a neutral diacyl lipid and/or a tocopherol; and (iv) a phospholipid. In one embodiment, the first and second compositions comprise (i) buprenorphine in the form of a free base or a pharmaceutically acceptable salt; (ii) 30 to 90% of a lipid matrix comprising at least one monoglyceride, at least one diglyceride, at least one triglyceride, at least one phospholipid, at least one tocopherol, or mixtures thereof; and (iii) 2% to 35% by weight an organic solvent selected from ethanol, propylene glycol, N-methyl-2-pyrrolidone, DMSO, and mixtures thereof. In embodiments, the first and second compositions comprise (i) buprenorphine in the form of a free base or a pharmaceutically acceptable salt; (ii) 30% to 90% by weight of at least one neutral diacyl lipid comprising diacyl glycerols and containing at least 50% of a glycerol dioleate; (iii) 10% to 60% by weight of at least one phospholipid having polar head groups consisting of at least 50% phosphatidylcholine; and (iv) 2-30% by weight of ethanol, N-methyl-2-pyrrolidone, or a combination thereof. Such compositions are described in U.S. Pat. No. 8,892,782 and US Publication No. 2013/0190341, the disclosures of which are incorporated by reference herein in their entirety.

The sustained-release buprenorphine formulation includes a flowable composition and an implant. The sustained-release buprenorphine formulation provides an in situ sustained release of buprenorphine. The flowable composition accomplishes the sustained release by producing the implant in situ. The implant has a low volume and provides a long term, therapeutic delivery of buprenorphine. The flowable composition enables subcutaneous formation of the implant in situ and causes little or no tissue necrosis.

Methods for making the sustained-release buprenorphine formulations described herein are known in the art and described, for example, in U.S. Pat. Nos. 8,921,387 and 8,975,270, the disclosures of which are incorporated by reference herein in their entirety. In particular, the flowable composition is produced by combining all of the components recited in each of Formulas A, B, C, and D. The flowable composition can be administered by a syringe and needle to a patient in need of treatment. Other buprenorphine formulations that may be used in the methods described herein can be prepared by other methods known in the art, such as those described in US Publication No. 2013/210853, US Publication No. 2013/0202658, and WO 2014/016428, the disclosure of which are incorporated by reference herein in their entirety.

EXAMPLES

The following examples are for illustrative purposes and are not intended to limit the scope of the disclosure.

Example 1

Formulation D (containing 200 mg/mL buprenorphine base in a form suitable for subcutaneous injection and allowing for the release of buprenorphine at therapeutic levels for at least 28 days) was used. Following administration of Formulation D, day-to-day compliance over the ensuing month would not be a potential issue as it is with existing products that are administered on a daily basis. Also, since Formulation D contains buprenorphine base in a sustained release delivery formulation, the safety profile and clinical efficacy of Formulation D are expected to be similar to that of sublingually administered buprenorphine (e.g., SUBUTEX®) and buprenorphine/naloxone treatments (e.g., SUBUXONE®).

The primary goal of this study was to develop a model-based approach to rationally support and justify the dose and dosing regimen of Formulation D in Phase 2 and 3 trials. For this purpose, a modeling strategy was implemented to characterize the population pharmacokinetics of buprenorphine and norbuprenorphine (major metabolite of buprenorphine), and to assess the relationship between buprenorphine and μORO. In addition, the relationship between plasma concentration, μORO, withdrawal symptoms and attenuation (i.e., blockade) of hydromorphone challenge agonist effects was explored. Trial simulations were used for predicting the expected μORO after repeated subcutaneous injections of different doses of Formulation D administered once monthly. The model-based approach aimed at determining the Formulation D dosage range that is expected to sustain a μORO level of 70% and to establish the corresponding levels of withdrawal symptoms suppression and blockade of the effects of exogenously administered opioids.

The study was a single-center, open-label, sequential cohort, single ascending-dose study. Thirty-six opioid-dependent (by Diagnostic and Statistical Manual of Mental Disorders, Fourth Edition, Text Revision criteria) subjects were randomized to receive Formulation D containing 50 mg buprenorphine, 100 mg buprenorphine, or 200 mg buprenorphine. Subjects in each cohort received a single subcutaneous dose of Formulation D on Day 1. On Day 1, blood samples for measuring plasma concentrations were drawn at 0.5, 1, 2, 4, 6, 8 and 12 hour post-dose, daily on Day 2 through Day 22, and on Days 25, 28, 31, 35, 42, 49, 56, 63, 70, 77, 84, 112, 140, and 150. Human ethylenedi-aminetetraacetic acid (EDTA) treated plasma samples were analyzed for buprenorphine and norbuprenorphine using a validated liquid chromatography coupled to tandem mass spectrometry (LC-MS/MS) method. Human plasma contain-ing buprenorphine, norbuprenorphine, and the internal stan-dards, buprenorphine-D4 and norbuprenorphine-D3, was extracted with an organic solvent mixture after the addition of sodium hydroxide solution (liquid-liquid extraction). After extraction, the extract was evaporated, reconstituted, and an aliquot was injected on a Sciex API 5000 LC-MS/MS equipped with an UPLC column. Quantitation was per-formed using separate weighted ($1/x2$ for buprenorphine and $1/x$ for norbuprenorphine) linear least squares regression analyses generated from fortified plasma calibration stan-dards prepared immediately prior to each run. The method was validated for specificity, linearity, lower limit of quan-titation, precision, accuracy, recovery and stability for a range of 0.0250 to 5.0 ng/mL for buprenorphine and 0.0200 to 4.00 ng/mL for norbuprenorphine based on the analysis of 0.500 ml of plasma. The overall precision for both analytes was better than 6.3%; the overall accuracy was within ±10.3%. The recoveries for both analytes and internal stan-dards were above 80%. The established short-term and long-term stability covered the maximum sample storage time (methods unpublished).

All data preparation, summary statistics (mean, median, standard deviation, and other measures, as appropriate), logistic regression analysis, report and graphical display presentation were performed using R (version 2.14.1) (Foundation for Statistical Computing (2009). R: a language and environment for statistical computing. website: www.R-project.org. Accessed 14 Dec. 2013). The population phar-macokinetic analysis was conducted using the NONMEM software, Version 7.2 (Beal et al, NONMEM user's guide, 1989-2013. Ellicott City: Icon Development Solutions; 2013). NONMEM was run in a Windows Vista operating system using the Fortran compiler gfortran version 4.6.0. Diagnostic graphics, exploratory analyses and post-process-ing of NONMEM outputs were performed using R and Xpose (version 4.3) (Parke et al, Comput Meth Prog Bio., 59:19-29 (1999)). The Perl based software Perl-speaks-NONMEM (PsN) (version 3.4.2) was used to perform bootstrapping and visual predictive checks (VPCs) (Ko-bayashi et al, Drug Metab Disp., 26:818-21 (1998)).

The first-order conditional estimation with interaction method (FOCE-I) was used for estimating the fixed and random effect parameters using a non-linear-mixed effect approach. Appropriateness of the model was evaluated using various goodness-of-fit criteria, including diagnostic scatter plots, likelihood-ratio-test (LRT), and measures of model stability and adequacy (successful convergence, significant digits, matrix singularity). The results for LRT were con-sidered statistically significant if decreases in the objective function value (OFV) of nested models were more than 3.84 (P<0.05, 1 degree of freedom) throughout the model build-ing process.

The inter-individual variability (IIV) on all the model parameters was assumed log-normally distributed. The residual variability, which was comprised of, but not limited to intra-individual variability, experimental errors, process noise and/or model misspecifications, was modeled using additive, proportional, and combined error structures.

An outlier was defined as an aberrant observation that significantly deviates from the rest of observations in a particular individual and did not refer to a subject as an outlier. The proportion of outliers in a dataset should be low and such points may be excluded from the analysis given the potential for these observations to negatively impact the convergence and/or parameter estimates (i.e., which may cause a bias) (Food and Drug Administration Guidance for Industry: Population Pharmacokinetics (1999)). Outlier detection was based initially on visual examination of indi-vidual and pooled pharmacokinetic profiles. Additionally, data points identified with an absolute conditional weighted residual (|CWRES|)>3 during the initial model building process were excluded from the analysis. The CWRES are weighted residuals calculated using the FOCE method and have been shown to represent a reliable estimate of the distribution of residuals (Hooker et al, Pharm Res, 24 (12): 2187-2197 (2007)). Given the theoretical distribution of CWRES, it is expected that 99.73% of the CWRES should lie in the interval-3, 3; for this reason, values outside this interval were considered as outliers.

Buprenorphine is metabolized primarily by cytochrome P450 3A4 to norbuprenorphine. Buprenorphine undergoes extensive first pass in the liver, thus it is administered sublingually with 50% to 60% bioavailability. The popula-tion pharmacokinetic model was developed to describe simultaneously the concentrations of buprenorphine and norbuprenorphine.

Age, sex, race, and dose were considered in the covariate analysis. Covariate model building was a step-wise process consisting of a forward and a backward selection procedure. The LRT was used to evaluate the significance of incorpo-rating or removing fixed effects in the population model based on alpha levels that were set a priori. Initially, each covariate was individually included in the base model. A covariate was retained in the model if a reduction in the objective function value (OFV) was ≥3.84 ($\chi^2$<0.05). After defining the full model, the significance of each covariate was tested individually by removing each one from the full model. A covariate was retained in the model if, upon removal, the OFV increased by more than 6.64 points ($\chi^2$<0.001).

A non-parametric bootstrap resampling method was used to evaluate the stability and robustness of the final pharma-cokinetic model (Parke et al, Comput Meth Prog Biomed, 59:19-29 (1999)). Resampling with replacement generated 100 bootstrap data sets and the final population pharmaco-kinetic model was fitted repeatedly to each of the 100 bootstrap data sets. The median and 95% confidence inter-vals of parameters obtained from this step were compared with the final parameter estimates. In addition, a VPC was also performed. Results from the VPC were assessed using graphical comparison of the appropriate 90% prediction intervals from simulated data with overlaid observed data from the original dataset.

It is recognized that the medication assisted treatment of opioid dependence is related to the opioid pharmacotherapy occupying brain μ-opioid receptors. The level of receptor occupancy is expected to mediate the abuse and dependence potential of opioids and to predict clinical efficacy. Specifi-cally, higher medication doses are hypothesized to decrease μ-opioid receptor availability (or "binding potential") and provide agonist replacement that minimizes withdrawal symptoms and prevents the reinforcing, euphoric, and other effects of abused opioids resulting greater clinic attendance (Greenwald et al, Neuropsychopharmacology, 28:2000-2009 (2003). Opioid withdrawal symptoms are the body's physical response to the absence of the opioid, which include muscle aches, restless anxiety, diarrhea, abdominal cramping, nausea and vomiting. In clinical trials, subjective opioid withdrawal scales are used to quantify these withdrawal effects. In addition, the blockade of hydromorphone challenge agonist effects is measured by subjective drug-effect assessments which often employ ratings on visual analog scales using adjectives that reflect abuse potential such as "liking" or "good effect". These measures are quantitative and exhibit dose-response sensitivity to opioid exposure.

The experimental individual values for buprenorphine plasma concentrations, μORO, opioid withdrawal syndrome, and opioid-like agonist effects were provided from two published clinical trials. In trial 1, 5 heroin-dependent subjects underwent buprenorphine induction from 4 mg/day on Day 1 to 16 mg/day by Day 7 and were maintained at 32 mg/day for 12 days. On the $8^{th}$ day of the maintenance period, subjects were challenged with the opioid agonist hydromorphone and subjective drug effects were ascertained, and on Day 9, blood samples for the measurement of buprenorphine and norbuprenorphine were collected following buprenorphine administration. On the $10^{th}$ and $11^{th}$ day of the maintenance period, opioid withdrawal symptoms were measured prior to buprenorphine administration and 1, 2, 3, 6, and 12 hours afterwards. On the $12^{th}$ and final day of the maintenance period, a positron emission tomography (PET) scan with $[^{11}C]$-carfentanil was administered 4 hours after buprenorphine administration to measure μORO. Subjects were titrated down to the subsequent maintenance periods at buprenorphine doses of 16 mg/day for 12 days, 2 mg/day for 12 days, and to 0 mg/day for 12 days. During each subsequent maintenance period subjects underwent the hydromorphone challenge, measurement of opioid withdrawal symptoms, and a PET scan (Greenwald et al, Neuropsychopharmacology, 28:2000-2009 (2003)).

In trial 2, 10 heroin-dependent subjects were initially maintained ≥2 weeks on 16 mg/day buprenorphine given as sublingual tablets. Plasma buprenorphine concentration, opioid withdrawal symptoms, and four hydromorphone challenges (to measure subjective opioid agonist drug effects) or four PET brain scans with $[^{11}C]$-carfentanil (to measure μORO) were conducted at 4, 28, 52, and 76 hours after the last daily buprenorphine dose. In addition to characterizing the relationship between buprenorphine plasma concentration and μORO, the study assessed the relationship between μORO and two key clinical effects—opioid withdrawal syndrome and blockade of hydromorphone agonist subjective drug effects (Greenwald et al, Biol Psychiatry, 61:101-110 (2007).

In both trials, opioid agonist and withdrawal symptoms were assessed by using an Opioid Symptom Questionnaire with 16 agonist and 16 withdrawal scale items. Each item was scored from 0 (not at all) to 4 (extremely), yielding total scores ranging from 0 to 64. Buprenorphine attenuation (blockade) of hydromorphone agonist effects was measured by six visual analog scales (VAS) ratings including: any drug effect, high, good drug effect, bad drug effect, stimulated, and sedated (Greenwald et al, Neuropsychopharmacology, 28:2000-2009 (2003); Greenwald et al, Biol Psychiatry, 61:101-110 (2007). From both trials, whole brain imaging results were used to calculate receptor μOR availability. Percent μORO was calculated as (100 minus μ-opioid receptor availability).

The analysis dataset included 36 subjects for a total of 2797 observations with 66 observations below the lower limit of quantification. These values were considered as missing in the NONMEM analysis. The buprenorphine and norbuprenorphine measurements were simultaneously fitted using the ADVAN5 TRANS1 routine in NONMEM. The absorption of Formulation D from the subcutaneous injection site was described by a dual model that was described by a first-order absorption process associated with the rapid absorption and the first observed peak; and a delayed delivery process that was described by a transit compartment absorption model to mimic the sustained-release components of Formulation D (Savic et al, J Pharmacokinet Pharmacodyn, 34:711-726 (2007). The disposition model was a one-compartment model with a first-order elimination, and first-order conversion to norbuprenorphine. This metabolite was subsequently distributed in a peripheral compartment and eliminated according to a first-order process.

Initial analysis of the distribution of the CWRES indicated that 28 observations showed an absolute CWRES >3. These values satisfied the definition of outlier measurements. Therefore, a new dataset was generated where these measurements were considered as missing observations.

The new analysis dataset included 36 subjects for a total of 2,769 observations. The buprenorphine and norbuprenorphine concentrations were again simultaneously fitted using the ADVAN5 TRANS1 routine in NONMEM. The residual error model included a combined additive (Add Err) and proportional components with a different proportional component for buprenorphine (Prop Err BUP) and for norbuprenorphine (Prop Err NorBUP). The results of this analysis were considered as the final model.

Overall, there was no apparent bias in the goodness-of-fit diagnostic plots and in the evaluation of the VPCs, suggesting that the final population pharmacokinetic model was adequate in describing the buprenorphine and norbuprenorphine plasma concentration-time courses at Formulation D doses of 50 mg buprenorphine, 100 mg buprenorphine, and 200 mg buprenorphine.

The high level of agreement between the parameter estimated by NONMEM and by the bootstrap procedure, together with the precision of the estimated parameters, supports the adequacy of the model to describe these data.

Empirical Bayesian estimates of individual parameters and random effects were obtained from the base model in the NONMEM analysis. The relationships between individual model parameters and the selected covariates were evaluated graphically. Inspection of the generated plots indicated a potential impact of sex on the volume of distribution for the central norbuprenorphine compartment $V_3$. This hypothesis was formally tested by incorporating sex as covariate of $V_3$ in the model. However, the resulting objective function did not show a significant change with respect to the base model. Overall, it was not possible to identify any covariate with significant impact on the population pharmacokinetic variability, given the relatively small number of subjects in the study.

A saturable $E_{max}$ model with an additive error model was used for describing the relationship between buprenorphine plasma concentrations and μORO as shown in Equation 1:

$$\mu ORO = \frac{E_{max} \bullet Cp}{EC_{50} + Cp} \qquad \text{(Equation 1)}$$

where Cp is buprenorphine plasma concentration and $EC_{50}$ is buprenorphine plasma concentration expected to achieve 50% of the maximal $\mu ORO$ ($E_{max}$). This model was developed assuming a direct relationship between plasma concentration and $\mu ORO$ without equilibration delay. This model assumes that the metabolite norbuprenorphine has negligible activity with respect to brain $\mu ORO$. The analysis dataset ($\mu ORO$ and buprenorphine pharmacokinetic sampling) included 15 subjects with a total of 59 pharmacokinetic/u ORO data. The modeling was performed using the FOCE-I method as implemented in the NONMEM software.

The estimated value for $E_{max}$ (standard error) was 91.4% (3.94) and the estimated value for $EC_{50}$ (standard error) was 0.67 (0.19) (ng/mL). The inter-individual variability of $E_{max}$ was not estimated due to the limited number of measures available in the proximity of the estimated $E_{max}$ value. The adequacy of the final model was evaluated using the visual predictive check method. Four-hundred replicates of the original dataset were simulated based on the final model, and a 90% prediction interval was computed based on the simulated datasets. The observed $\mu ORO$ versus the buprenorphine concentration data were plotted on the prediction interval to visually assess the concordance between the simulated and observed data. Statistics of interest including the median were calculated from the simulated and observed data for comparison. The median population prediction and distributions of quantiles ($5^{th}$, median, $95^{th}$) of simulated data were compared and found to be best described by a linear relationship between $\mu ORO$ and buprenorphine plasma concentrations up to 2 ng/mL. When buprenorphine levels approached 2-3 ng/mL, the $\mu ORO$ was saturated and reached a plateau with occupancy ranging between 70-90%. Greenwald et al, Biol Psychiatry, 61:101-110 (2007) suggests that the threshold for suppressing withdrawal and the blockade of agonist symptom effects is between 50-60% buprenorphine $\mu ORO$ while additional benefit and clinical efficacy was observed at 70% $\mu ORO$. As a result of these findings, a 70% $\mu ORO$ was the desired target. The predictive checks seems to indicate a larger variability in model predictions compared to observations at the saturation levels (e.g., above 3-4 ng/mL concentrations), and more data would be required to validate the model predictions for that concentration range.

Regression models were used to describe relationships between mean hydromorphone induced changes in agonist symptoms, mean withdrawal symptom scores, or mean buprenorphine plasma concentrations each with respect to the mean μ-opioid receptor availability. These data suggest that at a mean buprenorphine plasma concentration of 2 ng/ml is able to provide the desired 70% μ-opioid receptor occupancy. The same conditions are associated with low reported agonist drug effects and withdrawal symptoms (scores≤2). For the treatment of opioid dependence, the positive clinical outcomes are free of withdrawal, cravings and the drug-induced highs and lows of addiction. The individuals who exhibit greater μORO and more suppression of withdrawal symptoms experience better treatment outcomes (Greenwald et al, Imaging opioid receptors: applications to substance use disorders. In: Dean et al, editors. Opioid receptors and antagonists: from bench to clinic. New York: Humana Press, pages 45-65 (2009)). As buprenorphine plasma concentrations decline, there is a concomitant increase in subjective hydromorphone agonist drug effects and withdrawal symptoms with a corresponding decrease in μ-opioid receptor occupancy.

The simulated drug concentrations of buprenorphine and norbuprenorphine after repeated subcutaneous injections of Formulation D were derived from the final model parameter estimates. The 400 hypothetical subjects received 4 subcutaneous injections of Formulation D containing 50 mg, 100 mg buprenorphine, 200 mg buprenorphine, or 300 mg buprenorphine doses separated by 28 days. The objective of this simulation was to predict buprenorphine plasma concentrations after multiple doses of Formulation D and to consequently predict the corresponding μORO. Simulation indicated that the desired >70% receptor occupancy may be achieved after multiple doses of Formulation D containing 200 mg buprenorphine.

Example 2

This study implemented pharmacokinetic/pharmacodynamics (PK/PD) modeling to support the clinical development of Formulation D, a sustained-release formulation of buprenorphine for the treatment of opioid dependence. Such a formulation could offer advantages over existing buprenorphine pharmacotherapy by improving patient compliance and reducing the diversion of the product.

A population pharmacokinetic model was developed using 36 opioid-dependent subjects who received single subcutaneous doses of Formulation D. Another PK/PD model was developed using μ-opioid receptor occupancy data to predict efficacy of Formulation D after repeated doses. It was also assessed how buprenorphine plasma concentrations were correlated to opioid withdrawal symptoms and hydromorphone agonist blockade data from 15 heroin-dependent subjects.

The resulting pharmacokinetic model accurately described buprenorphine and norbuprenorphine plasma concentrations. A saturable maximum effect ($E_{max}$) model with 0.67 ng/ml effective concentration at 50% of maximum ($EC_{50}$) and 91% $E_{max}$ best described μORO versus buprenorphine plasma concentrations. Linear relationships were found among μORO, withdrawal symptoms, and blockade of agonist effects.

Previous published findings demonstrate μORO≥70% is needed to achieve withdrawal suppression and blockade of opioid agonist subjective effects. Model simulations indicated that Formulation D containing 200 mg buprenorphine should achieve 2-3 ng/ml buprenorphine average concentrations and desired efficacy.

This study demonstrated the relationship among buprenorphine plasma concentrations, μORO, and blockade of opioid agonist effects. A saturable $E_{max}$ model was established between buprenorphine plasma levels and μORO. The desired buprenorphine activity was achieved at μORO≥70%. A buprenorphine plasma concentration of 2 ng/mL is required to achieve a μORO of approximately 70%. This analysis provided new insight onto the long-acting pharmacokinetic and pharmacokinetic/μORO profile of Formulation D.

Example 3

As described in Examples 1 and 2, modeling showed that mu opioid receptor occupancy (RO)≥70% and buprenorphine plasma levels ≥2 ng/ml are needed to provide full blockade of opioid agonist effects (Nasser et al, Clin Pharmacokinet, 2014). This example was performed to assess Formulation D (containing 300 mg buprenorphine) blockade of hydromorphone-induced subjective and reinforcing effects, and to determine the accuracy of the modeling presented in Example A in a clinical setting.

A total of 39 subjects with moderate or severe opioid use disorder (not seeking treatment) first completed 3 hydromorphone challenges (0, 6, 18 mg intramuscular on 3 consecutive days in randomized order), then 3 hydromorphone challenges at the end of 14-day SUBOXONE® film stabilization. This was followed by two injections of Formulation D (containing 300 mg buprenorphine) separated by 28 days. For 12 weeks after the first Formulation D dose, on days 5-7 of each week, subjects received 3 hydromorphone challenges in randomized (6 sequences) order. A Drug Liking visual analog scale (VAS) score was the primary, and hydromorphone reinforcing effects (log breakpoint values), and VAS for Any Effect, Bad Effect, High, Good Effect, and Sedation were secondary endpoints. Statistical comparison using mixed effects model was used for each week. Change from hydromorphone 0 mg with 95% CI was reported, with a difference cut-off of less than or equal to 11 was required to declare full blockade. A PK sample was collected the morning of each hydromorphone administration day. The $E_{max}$ model of Equation 1 was used to calculate μ-opioid receptor occupancy.

For Drug Liking, mean differences for 6 or 18 mg hydromorphone compared to placebo were <7 units on week 1 and decreased over the 12 weeks. After the second Formulation D injection, the 95% CI of the difference included 0. Hydromorphone reinforcing effects and all VAS showed similar results. Buprenorphine concentrations were 1.8-3.7 ng/mL and the μ-opioid receptor occupancy was 65-76% over the 12 weeks.

At 300 mg of buprenorphine, Formulation D blocked hydromorphone subjective and reinforcing effects from weeks 1-12 in patients with moderate or severe opioid use disorder.

Example 4

Data were obtained from an open label, multiple dose study conducted in 89 treatment-seeking opioid-dependent subjects. Subjects were inducted and stabilized on SUBUTEX® (buprenorphine, Indivior UK Limited) at various doses (8-24 mg) before transitioning to Formulation D (50, 100, 200, or 300 mg) given as 4 subcutaneous monthly injections. A joint population PK model was developed from buprenorphine plasma concentrations measured after SUBUTEX® (buprenorphine, Indivior UK Limited) and treatment with Formulation D. Model simulations were conducted to assist dose selection and evaluate the impact of drug holidays. Prediction of μ-opioid receptors occupancy (μORO) was based on a previously developed PK/PD model (Nasser et al, Clin Pharmacokinet, 2014).

Modeling and simulation showed that a 300 mg dose of Formulation D every 28 days was appropriate for immediately achieving an effective exposure after the first SC injection and could maintain effective levels of exposure during chronic treatment. Furthermore, simulations indicated that in the unexpected event of two-week holiday the levels of μORO remained consistently above 80% with no significant loss of drug efficacy. The results of the analysis provided quantitative criteria for effective clinical dose selection and showed that a two-week drug holiday did not result in a loss of drug efficacy.

Example 5

A 6 month clinical study will be conducted to test two different dosage regimens of Formulation D on patients seeking treatment for opioid dependence. Patient Group 1 will be administered a 300 mg dose of buprenorphine base of Formulation D on Month 1 (day 1) and Month 2 (day 29), and will then be administered a 100 mg dose of buprenorphine base of Formulation D on Month 3 (day 57), Month 4 (day 85), Month 5 (day 113), and Month 6 (day 141). Patient Group 2 will be administered a 300 mg dose of buprenorphine base of Formulation D on each of Months 1, 2, 3, 4, 5, and 6. The pk/pD modeling analysis predicts that the average buprenorphine concentration ($C_{ave}$ in ng/mL) for each month for each group will be as follows:

TABLE 1

| | | Schedules for dosing regimen | | | | |
| --- | --- | --- | --- | --- | --- | --- |
| | Month 1 | Month 2 | Month 3 | Month 4 | Month 5 | Month 6 |
| Patient Group 1 | 1.9 | 3.1 | 3.0 | 3.0 | 2.8 | 2.6 |
| Patient Group 2 | 1.9 | 3.1 | 4.3 | 5.1 | 5.7 | 6.0 |

Study Design: This was an open-label, multiple dose study (NLM Identifier: NCT01738503). This study enrolled 89 treatment-seeking opioid-dependent subjects based on criteria from the Diagnostic and Statistical Manual of Mental Disorders, 4th Edition, Text Revision (DSM-IV-TR). Subjects were inducted and stabilized (over a 13-day period) on SUBUTEX® (buprenorphine sublingual tablet; Indivior, Richmond, VA) at doses of 8 mg, 12 mg, 14 mg, 24 mg, or 8-24 mg to receive Formulation D containing doses of 50 mg, 100 mg, or 200 mg buprenorphine in 4 subcutaneous (SC) injections separated by 28 days or 300 mg buprenorphine in 6 subcutaneous (SC) injections separated by 28 days. The 6 cohorts were defined as follows (the first dose is SUBUTEX® and the second dose is Formulation D): Cohort #1 (n=15) 8 mg+50 mg; Cohort #2 (n=15) 12 mg+100 mg; Cohort #3 (n=15) 24 mg+200 mg; Cohort #4 (n=15) 8 mg+100 mg; Cohort #5 (n=15) 14 mg+200 mg, and Cohort #6 (n=14) 8-24 mg+300 mg.

Blood Collection Schedule: Blood samples for buprenorphine PK assessments were collected during the SUBUTEX® stabilization period at pre-dose time on Day-7 to Day-1 then at 0.5, 1, 2, 4, 6, 8, 12, and 24 hours post-dose on Day-1. After the first Formulation D subcutaneous injection, blood samples were collected at 1, 2, 4, 6, 8, 12, 20, 24, 30, 48, 144, 192, 240, 312, 384, 456, 528, and 600 hours post-dose. During the second, third and fifth (300 mg dose) Formulation D subcutaneous injections, blood samples were collected at: pre-dose, 1, 12, 24, 48, 192, 312, and 456 hours post-dose. During the fourth Formulation D subcutaneous injection or the sixth Formulation D SC injection (300 mg dose only), blood samples were collected at: pre dose, 1, 2, 4, 6, 8, 12, 20, 24, 30, 48, 144, 192, 240, 312, 384, 456, 528, 600, 672, 864, 1008, 1200, and 1344 hours post-dose. The plasma samples were analyzed using a validated method of a liquid chromatography with tandem mass spectrometry (LC-MS/MS) for buprenorphine. The LLOQ for buprenorphine was 50 pg/mL.

Population pharmacokinetic analysis: A population PK model was developed to simultaneously describe the time course of the buprenorphine plasma concentrations after repeated doses of SUBUTEX® during the induction and stabilization period and the repeated SC injections of Formulation D. Circulating buprenorphine concentrations were calculated as the resultant of SUBUTEX® and Formulation D administrations. A total of 5498 observations obtained in 89 subjects were included in the population PK analysis.

Previously published models were selected as a starting point for model building. Nasser et al, Clin. Pharmacokinet, 53 (9): 813-824 (2014). The choice of the final models was based on the analysis of the semi-logarithmic scatter plots of the buprenorphine plasma concentrations versus time. After SUBUTEX® administration, the buprenorphine PK profile was best described by a two-compartment model with a first-order absorption rate constant (k12), a distribution in the peripheral compartment (rate constants k23 and k32) and a first-order elimination rate constant (k20).

After SC administration, Formulation D exhibited complex kinetics of buprenorphine with a prolonged plasma terminal half-life. The resulting PK time course suggested that the likely model accounted for a dual absorption process: the first one associated with a rapid delivery from the SC injection site (first-order absorption process) and the second one associated with the slow delivery from Formulation D (delayed delivery process described by a transit compartment absorption model8). In this model, kal is the first-order absorption rate constant characterizing buprenorphine immediately reaching the systemic circulation, ka2 is the first-order absorption rate constant characterizing the rate of buprenorphine entering into the transit compartment system, kk1 is the rate characterizing the delayed process in the transit compartments, k50 is the elimination rate constant of buprenorphine, and k56 and k65 are the transfer rate constants between the central and peripheral buprenorphine compartments. In this model S2 represents the volume of distribution of the central compartment for buprenorphine after SUBUTEX® administration and S5 represents the volume of distribution of buprenorphine after SC administration of Formulation D.

The buprenorphine plasma concentrations were modeled using the ADVAN6 routine in NONMEM software version 7.3. The stochastic approximation expectation-maximization (SAEM) with interaction computational algorithm was used for estimation of population PK model parameters. The maximum number of iterations in the stochastic phase (NBURN) of the SAEM method was 2000 followed by 500 iterations in the accumulation phase (NITER). Convergence was assessed visually based on SAEM convergence plots for the fixed and random effect parameters. The $-2$ log-likelihood ($-2$LL) value at the final model parameter estimates was calculated using the importance sampling approach (IMP) as implemented in NONMEM version 7.3.

Model selection was based on various goodness-of fit criteria, including standard diagnostic plots, likelihood-ratio-test (LRT), and visual predictive checks (VPC). The results for LRT were considered statistically significant if decreases in-2LL of nested models were more than 3.84 ($p<0.05$, one degree of freedom) throughout the model building process. The inter-individual variability (IIV) was modeled assuming a log-normal distribution for individual PK parameters. The relationship between a PK parameter (P) and the subject-specific random effect was expressed as:

$$P_j = P_{TV} e^{\eta p_j} \qquad \text{(Equation 2)}$$

where Pj is the value of the PK parameter for the jth individual, $P_{TV}$ is the typical value of P in the population, and $\eta p_j$ denotes the difference between Pj and $P_{TV}$. The random effects $\eta p_j$ were assumed to be independent and identically distributed with a mean of zero and variance of $\omega p^2$.

The residual variability, which comprised of, but was not limited to intra-individual variability, experimental errors, process noise and/or model misspecifications, was modeled using additive, proportional, and combined error structures. The "combined additive and proportional error" was retained in the final model.

Covariate Analysis. The following variables: age, BMI, Weight, Gender, Race, Ethnicity were prospectively identified as potential covariates. Covariate model building was a step-wise process consisting of a forward and a backward selection procedure. The LRT was used to evaluate the significance of incorporating or removing fixed effects into the population model based on alpha levels that were set a priori. Initially, each covariate was individually included in the base model. A covariate was retained into the model if a reduction in $-2$LL was $\geq 3.84$ ($\chi^2 < 0.05$). After the full model was defined, the significance of each covariate was tested individually by removing each one at the time from the full model. A covariate was retained in the model if, upon removal, the $-2$LL increased by more than 6.64 points ($\chi^2 < 0.001$).

Model Evaluation. Visual predictive checks (VPC) with 200 simulated datasets were used to assess the predictive performance of the model. Results from the VPC were assessed by graphical comparison of the medians and appropriate 90% prediction intervals calculated at each time point from the simulated data compared to observed data from the original dataset.

Assess clinical effective dose and evaluate the impact of missed doses on Formulation D PK and μORO. The level of μORO is recognized as one of the drivers of the clinical efficacy of buprenorphine. The currently accepted hypothesis is that the μORO should be greater than 70% to achieve optimal opioid blockade in the treatment of opioid use disorder. In a previous study, a population PK/μORO model was developed to fully characterize the relationship between buprenorphine plasma levels and μORO. Nasser et al, Clin. Pharmacokinet, 53 (9): 813-824 (2014). This relationship was best described by an Emax model with an EC50 of 0.67 ng/mL and an Emax of 91%. The rational for clinical dose selection of Formulation D was based on the evaluation of the dose appropriate for providing the target receptor occupancy. Furthermore, the dose selection criterion was also explored in the event a patient occasionally fails to take the prescribed dose at the prescribed time. For this purpose, additional simulations were conducted to evaluate the impact of the missed doses on Formulation D on the predicted μORO for repeated doses of 100 mg or 300 mg. For each dose level (100 mg or 300 mg), three scenarios were explored: Scenario 0: Reference scenario where a subject takes the dose at the prescribed time (once every 4 weeks); Scenario 1:1 SC injection of Formulation D, with 2-week holiday prior to the 2nd SC injection of Formulation D; Scenario 2:3 SC injections of Formulation D given at a 28-day interval, with 2-week holiday prior to the 4th SC injection of Formulation D.

For all scenarios, predictions of buprenorphine plasma concentrations and μORO were generated using the present population PK model and previously published PK/μORO model Greenwald et al, Neuropsychopharmacology, 28:2000-2009 (2003).

Software. All data preparation was performed using R (version 3.0.2). The population PK analysis was conducted using the NONMEM software, version 7.3. NONMEM was run in a Windows 8.1 operating system using the Fortran compiler gfortran version 4.6.0. Diagnostic graphics, exploratory analyses and post-processing of NONMEM outputs were performed using R and Xpose (version 4.3).

Subjects Characteristics. A total of 89 subjects were included in the analysis. The mean age was 33.8 year, mean weight was 72.5 kg and the mean BMI was 24.6 (mg/kg2). There were 26 females and 60 males in the study. The majority of the subjects were White (70%) with only 30% being Black or African American.

Final Population PK Model. Age was found to significantly affect k12 and BMI was found to significantly affect ka2. The covariate models used for AGE and BMI were:

$$k_{12} = \theta_{k12} \cdot e^{(-Age \cdot \theta_{Age})} \qquad \text{(Equation 3)}$$

$$k_{a2} = \theta_{ka2} \cdot e^{(-(BMI-24.64) \cdot \theta_{BMI})} \qquad \text{(Equation 4)}$$

where 24.64 represents the mean value of BMI in the study.

Overall, there was no apparent bias in the goodness-of-fit plots, suggesting that the final population PK model was adequate in describing the buprenorphine plasma concentration-time course.

The adequacy of the final model was evaluated using the VPC method. Two-hundred replicates of the original dataset were simulated based on the final population PK model, and the distribution of the simulated data was summarized at each time point by the median and 90% prediction interval (delineated by the 5th and 95th percentiles). The concordance between the observations and the simulated data (medians and 90% prediction intervals) was assessed graphically following normalization by the dose in order to present all the data on a same plot.

The VPC method for the SUBUTEX® pre-treatment and for Formulation D treatment show that the overall population PK model analyzing the buprenorphine time-course after the SUBUTEX® induction period and after the repeated SC injections of Formulation D performed well. Also, the variability in the data was well described by the model, although slightly overestimated for Formulation D. Altogether, the goodness-of-fit plots and VPC indicated that the population PK model properly described the observed data.

Dose selection and Impact of missed doses of Formulation D. Predicted time-courses of μORO for repeated SC injections of Formulation D at 50 mg, 100 mg, 200 mg and 300 mg reveal that a μORO greater than 70% would be achieved just after the first dose of 300 mg of Formulation D. This level is then maintained during chronic treatment. The target μORO level can also be reached with the dose of 200 mg. However, at this dose, the expected μORO will not reach the effective level during the first month of treatment. Altogether, these findings support the choice of 300 mg as a starting dose for treatment of opioid dependence.

The results of the simulations conducted for evaluating the potential impact of drug holiday found that in the case of repeated doses of 300 mg, the predicted levels of μORO after two-week holiday remained consistently above 80%, suggesting that the probability of lacking efficacy with Formulation D under these circumstances is extremely low.

The objective of this analysis was to develop a model-based approach to characterize the population PK of buprenorphine after multiple SC injections of 50 mg, 100 mg, 200 mg and 300 mg doses of Formulation D in treatment seeking opioid-dependent subjects who were inducted and then stabilized on a buprenorphine sublingual tablet (SUBUTEX®) dose of 8 mg, 12 mg, 14 mg or 24 mg prior to transfer. The secondary objective was to define the rationale for clinical dose selection and to evaluate the impact of missed doses on the expected level of Formulation D efficacy.

The analysis of the PK profile of buprenorphine after Formulation D administration revealed a complex and multi-phase absorption profile, with sustained buprenorphine plasma concentrations over the dosing interval. These distinguishing features of the PK of buprenorphine required the development of a complex PK model accounting for this absorption processes associated with Formulation D into the systemic circulation.

The mean transit time (defined as the number of transit compartments/kk1) associated with the slow release of buprenorphine from Formulation D could be estimated at ~5.5 weeks, which is the likely reason for the curvilinear shape of the plasma concentration-time profile. The results of the analysis confirmed earlier predictions of buprenorphine plasma exposures after repeated SC injections of Formulation D at the doses of 50 mg to 300 mg previously generated using single dose PK data. Nasser et al, Clin. Pharmacokinet, 53 (9): 813-824 (2014).

The model outcomes indicated that a linear and time invariant PK model is appropriate for characterizing the PK of buprenorphine and for predicting the exposure expected at different dosage regimens. The covariates analysis provided important insight into the absorption process of buprenorphine. BMI was identified as a statistically significant covariate affecting the absorption process of Formulation D. Patients with smaller BMI showed a higher rate of the absorption process associated with buprenorphine delivery from Formulation D (ka2). However, the rate of the immediate absorption (kal) was not affected by the BMI. For this reason the Cmax value of buprenorphine remained substantially invariant with respect to the BMI values. The absorption process of the sublingual administration of SUBUTEX® was found to be affected by age. The rate of absorption from the sublingual site to the systemic circulation (k12) decreased with the increase of age.

It is recognized that the efficacy of a buprenorphine treatment for opioid dependence is associated with μORO. In Greenwald et al, Neuropsychopharmacology, 28:2000-2009 (2003), a population PK/μORO model was developed using buprenorphine PK and ORO data collected in 15 heroin-dependent subjects (5 subjects receiving buprenorphine daily tablet doses of 32 mg, 16 mg or 2 mg, or placebo, and 10 subjects receiving a buprenorphine daily tablet dose of 16 mg). This study characterized the relationship between buprenorphine plasma concentrations, μORO and blockade of opioid agonist effects. A saturable maximum effect (Emax) model was established between buprenorphine plasma levels and μORO. This model showed a linear relationship between μORO up to the desired 70% receptor occupancy and buprenorphine concentrations up to approximately 2 ng/ml. At buprenorphine concentrations greater than 2 ng/mL, saturation occurred on μORO where a 4.5-fold increase in observed buprenorphine concentrations resulted in observed μORO between 70% and less than 90%. Thus, once μORO is saturated, increasing doses are not expected to exert any appreciable effect. A linear correlation was established between buprenorphine clinical efficacy (withdrawal suppression and blockade of hydromorphone agonist subjective effects) and μORO.

This previous PK/μORO model [Nasser et al, Clin. Pharmacokinet, 53 (9): 813-824 (2014)] together with the present population PK model were used to conduct simulations and predict μORO after repeated SC injections of Formulation D containing buprenorphine at doses of 50 mg, 100 mg, 200 mg and 300 mg. The results of the simulations provided quantitative criteria for the clinical dose selection for the late phase clinical development of Formulation D: the dose of 300 mg every 28 days was found to be appropriate for immediately achieving an effective exposure after the first SC injection and to maintain an effective level of exposure during chronic treatment. Furthermore, the results of the simulations conducted to evaluate the potential impact of holiday in drug intake indicated that in the unexpected event of one- or two-week holiday the level of μORO remained consistently above 80% for repeated doses of 300 mg. This finding indicates that significant loss of Formulation D efficacy may not be expected under these unexpected circumstances.

EMBODIMENTS

Embodiment 1. A method of treating opioid dependence or pain in a human in need thereof including the steps of: (a) administering a first composition including a dose of buprenorphine to the human once per month by injection for one month, two months, or three months; and thereafter (b) administering a second composition including a dose of buprenorphine to the human once per month by injection beginning with the second month, third month, or fourth month of administration, respectively, and for each month thereafter; to treat the opioid dependence or pain; wherein the amount of buprenorphine in the first composition is greater than the amount of buprenorphine in the second composition.

Embodiment 2. The method of Embodiment 1, wherein the first composition is administered to the human once per month for one month, and the second composition is administered to the human once per month beginning with the second month.

Embodiment 3. The method of Embodiment 1, wherein the first composition is administered to the human once per month for two months, and the second composition is administered to the human once per month beginning with the third month.

Embodiment 4. The method of Embodiment 1, wherein the first composition is administered to the human once per month for three months, and the second composition is administered to the human once per month beginning with the fourth month.

Embodiment 5. The method of Embodiment 1, wherein the first composition comprises from about 150 mg to about 500 mg buprenorphine, and the second composition comprises from about 10 mg to about 250 mg buprenorphine; and wherein the amount of buprenorphine in the first composition is greater than the amount of buprenorphine in the second composition.

Embodiment 6. The method of Embodiment 1, wherein the first composition comprises from 176 mg to about 500 mg buprenorphine, and the second composition comprises from about 10 mg to 175 mg buprenorphine.

Embodiment 7. The method of Embodiment 1, wherein the first composition comprises from about 200 mg to about 400 mg buprenorphine, and the second composition comprises from about 25 mg to 160 mg buprenorphine.

Embodiment 8. The method of Embodiment 1, wherein the first composition comprises from about 250 mg to about 350 mg buprenorphine, and the second composition comprises from about 50 mg to 150 mg buprenorphine.

Embodiment 9. The method of Embodiment 1, wherein the first composition comprises from about 280 mg to about 320 mg buprenorphine, and the second composition comprises from about 80 mg to 120 mg buprenorphine.

Embodiment 10. The method of Embodiment 1, wherein the first composition comprises about 300 mg buprenorphine, and the second composition comprises about 100 mg buprenorphine.

Embodiment 11. The method of any of Embodiments 1 to 10, wherein the buprenorphine is in the form of a free base.

Embodiment 12. The method of any of Embodiments 1 to 10, wherein the buprenorphine is in the form of a pharmaceutically acceptable salt.

Embodiment 13. The method of any one of Embodiments 1 to 12, wherein the method produces an average buprenorphine concentration of about 0.5 ng/ml to about 5 ng/ml in the human.

Embodiment 14. The method of any one of Embodiments 1 to 12, wherein the method produces an average buprenorphine concentration of about 1 ng/ml to about 4.5 ng/mL in the human.

Embodiment 15. The method of any one of Embodiments 1 to 12, wherein the method produces an average buprenorphine concentration of about 1.5 ng/ml to about 4 ng/mL in the human.

Embodiment 16. The method of any one of Embodiments 1 to 12, wherein the method produces an average buprenorphine concentration of about 1.5 ng/ml to about 3.5 ng/ml in the human.

Embodiment 17. The method of any one of Embodiments 1 to 12, wherein the method produces an average buprenorphine concentration of about 2 ng/mL to about 3 ng/mL in the human.

Embodiment 18. The method of any one of Embodiments 1 to 12, wherein the method produces an average buprenorphine concentration of about 2 ng/ml to about 4 ng/ml in the human.

Embodiment 19. The method of any one of Embodiments 1 to 12, wherein the method produces an average buprenorphine concentration of about 3 ng/ml to about 4 ng/mL in the human.

Embodiment 20. The method of any one of Embodiments 1 to 12, wherein the method produces an average buprenorphine concentration of about 1.8 ng/ml to about 3.7 ng/ml in the human.

Embodiment 21. The method of any one of Embodiments 13 to 20, wherein the average buprenorphine concentration is achieved from one to four months after the first injection.

Embodiment 22. The method of any one of Embodiments 13 to 20, wherein the average buprenorphine concentration is achieved from one to three months after the first injection.

Embodiment 23. The method of any one of Embodiments 13 to 20, wherein the average buprenorphine concentration is achieved from one to two months after the first injection.

Embodiment 24. The method of any one of Embodiments 13 to 20, wherein the average buprenorphine concentration is achieved within two months after the first injection.

Embodiment 25. The method of any one of Embodiments 13 to 20, wherein the average buprenorphine concentration is achieved within one month after the first injection.

Embodiment 26. The method of any one of Embodiments 1 to 13, wherein the method produces a μ-opioid receptor occupancy (as measured by a maximum effect model of Equation 1) greater than 60% in the human.

Embodiment 27. The method of any one of Embodiments 1 to 13, wherein the method produces a μ-opioid receptor occupancy (as measured by a maximum effect model of Equation 1) of at least 70%.

Embodiment 28. The method of any one of Embodiments 1 to 13, wherein the method produces a μ-opioid receptor occupancy (as measured by a maximum effect model of Equation 1) of greater than 60% to about 90%.

Embodiment 29. The method of any one of Embodiments 1 to 13, wherein the method produces a μ-opioid receptor occupancy (as measured by a maximum effect model of Equation 1) of about 65% to about 85%.

Embodiment 30. The method of any one of Embodiments 1 to 13, wherein the method produces a μ-opioid receptor occupancy (as measured by a maximum effect model of Equation 1) of about 65% to about 80%.

Embodiment 31. The method of any one of Embodiments 1 to 13, wherein the method produces a μ-opioid receptor occupancy (as measured by a maximum effect model of Equation 1) of about 65% to about 76%.

Embodiment 32. The method of any one of Embodiments 1 to 13, wherein the method produces a μ-opioid receptor occupancy (as measured by a maximum effect model of Equation 1) of about 65% to about 75%.

Embodiment 33. The method of any one of Embodiments 26 to 32, wherein the μ-opioid receptor occupancy is achieved from one to four months after the first injection.

Embodiment 34. The method of any one of Embodiments 26 to 32, wherein the μ-opioid receptor occupancy is achieved from one to three months after the first injection.

Embodiment 35. The method of any one of Embodiments 26 to 32, wherein the μ-opioid receptor occupancy is achieved from one to two months after the first injection.

Embodiment 36. The method of any one of Embodiments 26 to 32, wherein the μ-opioid receptor occupancy is achieved within two months after the first injection.

Embodiment 37. The method of any one of Embodiments 26 to 32, wherein the μ-opioid receptor occupancy is achieved within one month after the first injection.

Embodiment 38. The method of any one of Embodiments 1 to 37, wherein the injection is a subcutaneous injection.

Embodiment 39. The method of any one of Embodiments 1 to 38, wherein a month is from 28 days to 31 days.

Embodiment 40. The method of any one of Embodiments 1 to 38, wherein a month is 28 days.

Embodiment 41. The method of any one of Embodiments 1 to 40 for treating opioid dependence in the human in need thereof.

Embodiment 42. The method of Embodiment 41, wherein the method of treating opioid dependence is a method of suppressing opioid withdrawal signs and symptoms.

Embodiment 43. The method of any one of Embodiments 1 to 40 for treating pain in the human in need thereof.

Embodiment 44. The method of any one of Embodiments 1 to 10, wherein the first composition and the second composition each comprises, consists essentially of, or consists of: (i) about 18 wt % buprenorphine in the form of the free base; (ii) about 32 wt % of a 50:50 poly(DL-lactide-co-glycolide) copolymer having an average molecular weight of about 5,000 Daltons to about 25,000 Daltons; and (iii) about 50 wt % of N-methyl-2-pyrrolidone.

Embodiment 45. The method of any one of Embodiments 1 to 10, wherein the first composition and the second composition each comprises, consists essentially of, or consists of: (i) about 14 wt % to about 22 wt % buprenorphine in the form of the free base; (ii) about 22 wt % to about 42 wt % of a 50:50 to 80:20 poly(DL-lactide-co-glycolide) copolymer having an average molecular weight of about 5,000 Daltons to about 30,000 Daltons; and (iii) about 40 wt % to about 60 wt % of N-methyl-2-pyrrolidone.

Embodiment 46. The method of any one of Embodiments 1 to 10, wherein the first composition and the second composition each comprises, consists essentially of, or consists of: (i) about 10 wt % to about 30 wt % buprenorphine in the form of the free base; (ii) about 10 wt % to about 60 wt % of a 50:50 to 95:5 poly(DL-lactide-co-glycolide) copolymer having an average molecular weight of about 5,000 Daltons to about 40,000 Daltons; and (iii) about 30 wt % to about 70 wt % of N-methyl-2-pyrrolidone.

Embodiment 47. The method of any one of Embodiments 1 to 10, wherein the first composition and the second composition each includes, consists essentially of, or consists of: (i) at least one biodegradable thermoplastic polymer; (ii) at least one organic liquid which comprises an amide, an ester, a carbonate, a ketone, a lactam, an ether, a sulfonyl, or a combination thereof; and (iii) buprenorphine in the form of a free base or pharmaceutically acceptable salt.

Embodiment 48. The method of Embodiment 47, wherein the buprenorphine in the form of a free base or pharmaceutically acceptable salt is present in the first composition and/or the second composition in an amount between about 5 wt % to about 30 wt % or in an amount between about 10 wt % and about 25 wt %.

Embodiment 49. The method of Embodiment 47, wherein the buprenorphine in the form of a free base or pharmaceutically acceptable salt is present in the first composition and/or the second composition in an amount between about 15 wt % and about 20 wt %.

Embodiment 50. The method of Embodiment 47, wherein the organic liquid is present in the first composition and/or the second composition in an amount of about 30 wt % to about 70 wt %.

Embodiment 51. The method of Embodiment 47, wherein the organic liquid is present in the first composition and/or the second composition in an amount of about 40 wt % to about 60 wt %.

Embodiment 52. The method of Embodiment 47, wherein the organic liquid is N-methyl-2-pyrrolidone, 2-pyrrolidone, propylene glycol, polyethylene glycol, ethanol, acetone, tetrahydrofurfuryl alcohol, dimethyl isosorbide, acetic acid, lactic acid, methyl lactate, ethyl lactate, monomethyl succinate acid, monomethyl citric acid, glycofurol, glycerol formal, isopropylidene glycol, 2,2-dimethyl-1,3-dioxolone-4-methanol, dimethylformamide, dimethylacetamide, N,N-dimethylformamide, propylene carbonate, triacetin, dimethylsulfoxide, dimethylsulfone, epsilon-caprolactone, butyrolactone, caprolactam, and a mixture of two or more thereof.

Embodiment 53. The method of Embodiment 47, wherein the organic liquid is N-methyl-2-pyrrolidone, 2-pyrrolidone, N,N-dimethylformamide, dimethyl sulfoxide, propylene carbonate, caprolactam, polyethylene glycol, ethanol, or a mixture of two or more thereof.

Embodiment 54. The method of Embodiment 47, wherein the organic liquid is N-methyl-2-pyrrolidone.

Embodiment 55. The method of Embodiment 47, wherein the biodegradable thermoplastic polymer is present in the first composition and/or the second composition in an amount of about 10 wt % to about 60 wt %.

Embodiment 56. The method of Embodiment 47, wherein the biodegradable thermoplastic polymer is present in the first composition and/or the second composition in an amount of about 20 wt % to about 40 wt %.

Embodiment 57. The method of Embodiment 47, wherein the polymer is a polylactide, a polyglycolide, a polycaprolactone, a copolymer thereof, a terpolymer thereof, any combination thereof, or a mixture of two or more thereof.

Embodiment 58. The method of Embodiment 47, wherein the polymer is a poly(DL-lactide-co-glycolide) copolymer.

Embodiment 59. The method of Embodiment 47, wherein the polymer has an average molecular weight of about 5,000 Daltons to about 40,000 Daltons.

Embodiment 60. The method of Embodiment 47, wherein the polymer has an average molecular weight of about 5,000 Daltons to about 30,000 Daltons.

Embodiment 61. The method of Embodiment 47, wherein the polymer has an average molecular weight of about 5,000 Daltons to about 20,000 Daltons.

Embodiment 62. The method of Embodiment 47, wherein the polymer has an average molecular weight of about 10,000 Daltons to about 20,000 Daltons.

Embodiment 63. The method of Embodiment 58, wherein the poly(DL-lactide-co-glycolide) copolymer is a 50:50 to 95:5 poly(DL-lactide-co-glycolide) copolymer.

Embodiment 64. The method of Embodiment 58, wherein the poly(DL-lactide-co-glycolide) copolymer is a 50:50 to 80:20 poly(DL-lactide-co-glycolide) copolymer.

Embodiment 65. The method of Embodiment 58, wherein the poly(DL-lactide-co-glycolide) copolymer is a 50:50 poly(DL-lactide-co-glycolide) copolymer.

Embodiment 66. The method of Embodiment 58, wherein the poly(DL-lactide-co-glycolide) copolymer is a 50:50 poly(DL-lactide-co-glycolide) copolymer having an average molecular weight from about 5,000 Daltons to about 20,000 Daltons.

Embodiments for practicing the invention have been described. It will be understood and readily apparent to the skilled artisan that changes and modifications may be made to the embodiments described herein without departing from the spirit and the scope of the invention.

What is claimed is:

1. A method of treating moderate to severe opioid use disorder in an opioid-dependent human, the method comprising:
  (a) administering to said opioid-dependent human, by subcutaneous injection once per month for a period of one to three months, a first composition comprising:
    (i) about 14 wt % to about 22 wt % buprenorphine in the form of the free base;
    (ii) about 22 wt % to about 42 wt % of a 50:50 to 80:20 poly(DL-lactide-co-glycolide) copolymer having an average molecular weight of about 5,000 Daltons to about 30,000 Daltons; and
    (iii) about 40 wt % to about 60 wt % of N-methyl-2-pyrrolidone; and
  (b) administering to said opioid-dependent human, by subcutaneous injection once per month beginning one month after the last dose of the first composition, a second composition comprising:
    (i) about 14 wt % to about 22 wt % buprenorphine in the form of the free base;
    (ii) about 22 wt % to about 42 wt % of a 50:50 to 80:20 poly(DL-lactide-co-glycolide) copolymer having an average molecular weight of about 5,000 Daltons to about 30,000 Daltons; and
    (iii) about 40 wt % to about 60 wt % of N-methyl-2-pyrrolidone,
  wherein the amount of buprenorphine in (a)(i) is greater than the amount of buprenorphine in (b)(i).

2. The method according to claim 1, wherein the amount of buprenorphine in (a)(i) is about 250 mg to about 350 mg.

3. The method according to claim 2, wherein the amount of buprenorphine in (b)(i) is about 80 mg to about 120 mg.

4. The method according to claim 1, wherein the amount of buprenorphine in (b)(i) is about 80 mg to about 120 mg.

5. The method according to claim 1, wherein the amount of buprenorphine in (b)(i) is about 300 mg.

6. The method according to claim 1, wherein the amount of buprenorphine in (b)(i) is 300 mg.

7. The method according to claim 1, wherein the amount of buprenorphine in (b)(i) is about 100 mg.

8. The method according to claim 2, wherein the amount of buprenorphine in (b)(i) is about 100 mg.

9. The method according to claim 2, wherein the amount of buprenorphine in (b)(i) is about 300 mg.

* * * * *